US012178458B1

(12) United States Patent
Betelia et al.

(10) Patent No.: US 12,178,458 B1
(45) Date of Patent: Dec. 31, 2024

(54) GUIDEWIRELESS SHOCK WAVE CATHETERS

(71) Applicant: Shockwave Medical, Inc., Santa Clara, CA (US)

(72) Inventors: Rainier Betelia, San Jose, CA (US); Todd Weston Jenkins, Mountain View, CA (US); Danielle Sheree Rond, Santa Clara, CA (US); John Barritt, San Jose, CA (US); Kevin Nunes, Santa Clara, CA (US); Huy Phan, Santa Clara, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 0 days.

(21) Appl. No.: 18/666,301

(22) Filed: May 16, 2024

(51) Int. Cl.
*A61B 17/22* (2006.01)
*A61B 18/26* (2006.01)
*A61M 25/00* (2006.01)

(52) U.S. Cl.
CPC .......... *A61B 17/2202* (2013.01); *A61B 18/26* (2013.01); *A61M 25/005* (2013.01); *A61B 2017/22021* (2013.01); *A61B 2017/22025* (2013.01); *A61B 2017/22051* (2013.01); *A61B 2018/263* (2013.01)

(58) Field of Classification Search
CPC ................ A61B 17/2202; A61B 18/26; A61B 2017/22021; A61B 2017/22025; A61B 2017/22051; A61B 2018/263; A61M 25/005
See application file for complete search history.

(56) References Cited

U.S. PATENT DOCUMENTS

| 2,916,647 A | 12/1959 | George |
| 3,412,288 A | 11/1968 | Ostrander |
| 3,413,976 A | 12/1968 | Roze |
| 3,524,101 A | 8/1970 | Barbini |
| 3,583,766 A | 6/1971 | Padberg |

(Continued)

FOREIGN PATENT DOCUMENTS

| AU | 2009313507 B2 | 11/2014 |
| AU | 2013284490 B2 | 5/2018 |

(Continued)

OTHER PUBLICATIONS

Unpublished U.S. Appl. No. 18/595,148, internationally filed Mar. 4, 2024, titled "Burst Mode Operation of Intravascular Lithotripsy (IVL),".

*Primary Examiner* — Scott M. Getzow
(74) *Attorney, Agent, or Firm* — Morrison & Foerster LLP

(57) ABSTRACT

Various shock wave catheters and methods of use thereof that do not utilize a guidewire are described herein. The shock wave catheters include at least one shock wave emitter disposed within a distal portion of the shock wave catheter and configured to generate shock waves. The ends of conductive wires extending within an elongate tube can form the shock wave emitter(s). The shock wave emitter(s) can be surrounded by an enclosure fillable with a conductive fluid delivered by the lumen of the elongate tube. The elongate tube can include a coil or slits therein that enable flexibility of the shock wave catheter, which, in combination with the narrow profile of the shock wave catheters described herein, enable their use in navigating and treating small, tortuous vessels.

30 Claims, 25 Drawing Sheets

(56) References Cited

U.S. PATENT DOCUMENTS

| | | | |
|---|---|---|---|
| 3,785,382 A | 1/1974 | Schmidt-Kloiber et al. |
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,741,405 A | 5/1988 | Moeny et al. |
| 4,809,682 A | 3/1989 | Forssmann et al. |
| 4,813,934 A | 3/1989 | Engelson et al. |
| 4,878,495 A | 11/1989 | Grayzei |
| 4,890,603 A | 1/1990 | Filler |
| 4,900,303 A | 2/1990 | Lemelson |
| 4,990,134 A | 2/1991 | Auth |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,804 A | 4/1992 | Abele et al. |
| 5,116,227 A | 5/1992 | Levy |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,454,809 A | 10/1995 | Janssen |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,709,676 A | 1/1998 | Alt |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,309,324 B2 | 12/2007 | Hayes et al. |
| 7,389,148 B1 | 6/2008 | Morgan |
| 7,505,812 B1 | 3/2009 | Eggers et al. |
| 7,569,032 B2 | 8/2009 | Naimark et al. |
| 7,850,685 B2 | 12/2010 | Kunis et al. |
| 7,853,332 B2 | 12/2010 | Olsen et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Hakala et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,579,114 B2 | 2/2017 | Mantell et al. |
| 9,642,673 B2 | 5/2017 | Adams et al. |
| 9,730,715 B2 | 8/2017 | Adams |
| 9,993,292 B2 | 6/2018 | Adams et al. |
| 10,039,561 B2 | 8/2018 | Adams et al. |
| 10,118,015 B2 | 11/2018 | De La Rama et al. |
| 10,149,690 B2 | 12/2018 | Hawkins et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,226,265 B2 | 3/2019 | Ku et al. |
| 10,420,569 B2 | 9/2019 | Adams |
| 10,517,620 B2 | 12/2019 | Adams |
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Hawkins et al. |
| 10,709,462 B2 | 7/2020 | Nguyen et al. |
| 10,959,743 B2 | 3/2021 | Adams et al. |
| 10,966,737 B2 | 4/2021 | Nguyen |
| 10,973,538 B2 | 4/2021 | Hakala et al. |
| 11,000,299 B2 | 5/2021 | Hawkins et al. |
| 11,020,135 B1 * | 6/2021 | Hawkins ............ A61M 25/104 |
| 11,076,874 B2 | 8/2021 | Hakala et al. |
| 11,337,713 B2 | 5/2022 | Nguyen et al. |

(56) References Cited

U.S. PATENT DOCUMENTS

| | | |
|---|---|---|
| 11,432,834 B2 | 9/2022 | Adams |
| 11,534,187 B2 | 12/2022 | Bonutti |
| 11,596,424 B2 | 3/2023 | Hakala et al. |
| 11,622,780 B2 | 4/2023 | Nguyen et al. |
| 11,696,799 B2 | 7/2023 | Adams et al. |
| 11,771,449 B2 | 10/2023 | Adams et al. |
| 11,826,092 B2 | 11/2023 | McCaffrey et al. |
| 12,048,445 B2 | 7/2024 | Mantell |
| 2001/0044596 A1 | 11/2001 | Jaafar |
| 2002/0045890 A1 | 4/2002 | Celliers et al. |
| 2002/0082553 A1 | 6/2002 | Duchamp |
| 2002/0177889 A1 | 11/2002 | Brisken et al. |
| 2003/0004434 A1 | 1/2003 | Greco et al. |
| 2003/0009157 A1* | 1/2003 | Levine .................. A61B 18/26 606/7 |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0074484 A1 | 4/2006 | Huber |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2010/0016862 A1 | 1/2010 | Hawkins et al. |
| 2010/0036294 A1 | 1/2010 | Hawkins et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall et al. |
| 2012/0157991 A1 | 6/2012 | Christian |
| 2012/0203255 A1 | 8/2012 | Hawkins et al. |
| 2012/0253358 A1 | 10/2012 | Golan et al. |
| 2013/0030431 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0253622 A1 | 9/2013 | Hooven |
| 2014/0046229 A1 | 2/2014 | Hawkins et al. |
| 2014/0214061 A1 | 7/2014 | Adams et al. |
| 2015/0320432 A1 | 11/2015 | Adams |
| 2016/0151081 A1 | 6/2016 | Adams et al. |
| 2016/0324534 A1 | 11/2016 | Hawkins et al. |
| 2017/0135709 A1 | 5/2017 | Nguyen et al. |
| 2017/0311965 A1 | 11/2017 | Adams |
| 2019/0388110 A1 | 12/2019 | Nguyen et al. |
| 2021/0085347 A1 | 3/2021 | Phan et al. |
| 2021/0085383 A1 | 3/2021 | Vo et al. |
| 2021/0338258 A1 | 11/2021 | Hawkins et al. |
| 2022/0015785 A1 | 1/2022 | Hakala et al. |
| 2022/0183708 A1* | 6/2022 | Phan .................... A61B 17/225 |
| 2022/0240958 A1 | 8/2022 | Nguyen et al. |
| 2023/0043475 A1 | 2/2023 | Adams |
| 2023/0110647 A1 | 4/2023 | Buscaglia et al. |
| 2023/0123003 A1 | 4/2023 | Vo |
| 2023/0130458 A1* | 4/2023 | Walzman ....... A61B 17/320758 606/41 |
| 2023/0293197 A1 | 9/2023 | Nguyen et al. |
| 2023/0310073 A1 | 10/2023 | Adams et al. |
| 2023/0329731 A1 | 10/2023 | Hakala et al. |
| 2023/0380849 A1 | 11/2023 | Adams et al. |
| 2024/0099773 A1* | 3/2024 | Schabert .......... A61B 17/22012 |

FOREIGN PATENT DOCUMENTS

| | | |
|---|---|---|
| CA | 2104414 A1 | 2/1995 |
| CN | 1204242 A | 1/1999 |
| CN | 1269708 A | 10/2000 |
| CN | 1942145 A | 4/2007 |
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| CN | 203564304 U | 4/2014 |
| DE | 3038445 A1 | 5/1982 |
| DE | 202006014285 U1 | 12/2006 |
| EP | 0442199 A2 | 8/1991 |
| EP | 0571306 A1 | 11/1993 |
| EP | 623360 A | 11/1994 |
| EP | 0647435 A1 | 4/1995 |
| EP | 2253884 A1 | 11/2010 |
| EP | 2362798 B1 | 4/2014 |
| JP | S62-099210 U | 6/1987 |
| JP | S62-275446 A | 11/1987 |
| JP | H03-63059 A | 3/1991 |
| JP | H06-125915 A | 5/1994 |
| JP | H07-47135 A | 2/1995 |
| JP | H08-89511 A | 4/1996 |
| JP | H10-99444 A | 4/1998 |
| JP | H10-314177 A | 12/1998 |
| JP | H10-513379 A | 12/1998 |
| JP | 2002538932 A | 11/2002 |
| JP | 2004081374 A | 3/2004 |
| JP | 2004357792 A | 12/2004 |
| JP | 2005501597 A | 1/2005 |
| JP | 2005095410 A | 4/2005 |
| JP | 2005515825 A | 6/2005 |
| JP | 2006516465 A | 7/2006 |
| JP | 2007289707 A | 11/2007 |
| JP | 2007532182 A | 11/2007 |
| JP | 2008506447 A | 3/2008 |
| JP | 2011513694 A | 4/2011 |
| JP | 2011520248 A | 7/2011 |

(56) References Cited

FOREIGN PATENT DOCUMENTS

| | | |
|---|---|---|
| JP | 2011524203 A | 9/2011 |
| JP | 2011528963 A | 12/2011 |
| JP | 2012505050 A | 3/2012 |
| JP | 2012508042 A | 4/2012 |
| JP | 2015525657 A | 9/2015 |
| JP | 2015528327 A | 9/2015 |
| JP | 6029828 B2 | 11/2016 |
| JP | 6081510 B2 | 2/2017 |
| WO | WO-1989011307 A1 | 11/1989 |
| WO | WO-1996024297 A1 | 8/1996 |
| WO | WO-1999000060 A1 | 1/1999 |
| WO | WO-1999002096 A1 | 1/1999 |
| WO | WO-2000056237 A2 | 9/2000 |
| WO | WO-2004069072 A2 | 8/2004 |
| WO | WO-2005099594 A1 | 10/2005 |
| WO | WO-2005102199 A1 | 11/2005 |
| WO | WO-2006006169 A2 | 1/2006 |
| WO | WO-2006127158 A2 | 11/2006 |
| WO | WO-2007088546 A2 | 8/2007 |
| WO | WO-2007149905 A2 | 12/2007 |
| WO | WO-2009121017 A1 | 10/2009 |
| WO | WO-2009126544 A1 | 10/2009 |
| WO | WO-2009136268 A1 | 11/2009 |
| WO | WO-2009152352 A2 | 12/2009 |
| WO | WO-2010014515 A2 | 2/2010 |
| WO | WO-2010054048 A2 | 9/2010 |
| WO | WO-2011006017 A1 | 1/2011 |
| WO | WO-2011094111 A2 | 8/2011 |
| WO | WO-2011143468 A2 | 11/2011 |
| WO | WO-2012025833 A2 | 3/2012 |
| WO | WO-2013059735 A1 | 4/2013 |
| WO | WO-2014025397 A1 | 2/2014 |
| WO | WO-2014025620 A1 | 2/2014 |
| WO | WO-2015017499 A1 | 2/2015 |
| WO | WO-2019099218 A1 | 5/2019 |

* cited by examiner

GUIDEWIRELESS SHOCK WAVE CATHETERS

FIELD OF THE DISCLOSURE

The present disclosure relates generally to the field of medical devices and methods, and more specifically to shock wave catheters for treating calcified lesions in body lumens, such as calcified lesions and occlusions in vasculature and kidney stones in the urinary system.

BACKGROUND

A wide variety of catheters have been developed for treating calcified lesions, such as calcified lesions in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guidewire until the balloon is aligned with calcified plaques. The balloon is then pressurized (normally to greater than 10 atm), causing the balloon to expand in a vessel to push calcified plaques back into the vessel wall and dilate occluded regions of vasculature.

More recently, the technique and treatment of intravascular lithotripsy (IVL) has been developed, which is an interventional procedure to modify calcified plaque in diseased arteries. The mechanism of plaque modification is through use of a catheter having one or more acoustic shock wave generating sources located within a liquid that can generate acoustic shock waves that modify the calcified plaque. IVL devices vary in design with respect to the energy source used to generate the acoustic shock waves, with two exemplary energy sources being electrohydraulic generation and laser generation.

For electrohydraulic generation of acoustic shock waves, a conductive solution (e.g., saline) may be contained within an enclosure that surrounds electrodes or can be flushed through a tube that surrounds the electrodes. The calcified plaque modification is achieved by creating acoustic shock waves within the catheter by an electrical discharge across the electrodes. The energy from this electrical discharge enters the surrounding fluid faster than the speed of sound, generating an acoustic shock wave. In addition, the energy creates one or more rapidly expanding and collapsing vapor bubbles that generate secondary shock waves. The shock waves propagate radially outward and modify calcified plaque within the blood vessels. For laser generation of acoustic shock waves, a laser pulse is transmitted into and absorbed by a fluid within the catheter. This absorption process rapidly heats and vaporizes the fluid, thereby generating the rapidly expanding and collapsing vapor bubble, as well as the acoustic shock waves that propagate outward and modify the calcified plaque. The acoustic shock wave intensity is higher if a fluid is chosen that exhibits strong absorption at the laser wavelength that is employed. These examples of IVL devices are not intended to be a comprehensive list of potential energy sources to create IVL shock waves.

The IVL process may be considered different from standard atherectomy procedures in that it cracks calcium but does not liberate the cracked calcium from the tissue. Hence, generally speaking, IVL should not require aspiration nor embolic protection. Further, due to the compliance of a normal blood vessel and non-calcified plaque, the shock waves produced by IVL do not modify the normal vessel tissue or non-calcified plaque. Moreover, IVL does not carry the same degree of risk of perforation, dissection, or other damage to vasculature as atherectomy procedures or angioplasty procedures using cutting or scoring balloons.

More specifically, catheters to deliver IVL therapy have been developed that include pairs of electrodes for electrohydraulically generating shock waves inside an angioplasty balloon. Shock wave devices can be particularly effective for treating calcified plaque lesions because the acoustic pressure from the shock waves can crack and disrupt lesions near the angioplasty balloon without harming the surrounding tissue. In these devices, the catheter is advanced over a guidewire through a patient's vasculature until it is positioned proximal to and/or aligned with a calcified plaque lesion in a body lumen. The balloon is then inflated with conductive fluid (using a relatively low pressure of 2-4 atm) so that the balloon expands to contact the lesion but is not an inflation pressure that substantively displaces the lesion. Voltage pulses can then be applied across the electrodes of the electrode pairs to produce acoustic shock waves that propagate through the walls of the angioplasty balloon and into the lesions. Once the lesions have been cracked by the acoustic shock waves, the balloon can be expanded further to increase the cross-sectional area of the lumen and improve blood flow through the lumen. Alternative devices to deliver IVL therapy can be within a closed volume other than an angioplasty balloon, such as a cap, balloons of variable compliancy, or other enclosure.

Treatment of an occluded region of a vessel with a shock wave device typically involves a surgeon passing a guidewire through the vessel, including through the occluded region. The guidewire is typically narrow (e.g., as small as about 0.35 mm in diameter) and has a soft flexible tip to avoid penetrating the vessel wall while traversing the vessel. Once the guidewire has been passed through the occlusion, the angioplasty balloon is then fed along the guidewire to the location of the occlusion. Unfortunately, in situations in which the vessel is completely, or almost completely, occluded (e.g., a chronic total occlusion), even the guidewire cannot pass through the occlusion. For example, the occlusion can be too tight and solid for the soft guidewire to pass through it. Stiffer guidewires could be used in these scenarios, but they increase the risk of the guidewire penetrating the vessel wall. Guidewires have been proposed that utilize radiofrequency energy to open an occlusion as the guidewire is passed through the occluded vessel. However, the heat generated by the radiofrequency energy is often too intense, risking damage to the walls of the vessel. The difficulties with passing guidewires through occlusions become even greater when the occluded vessel is narrow and/or tortuous. Surgeons must use extreme caution in such scenarios and must continuously move the guidewire, without pause, to avoid vessel damage.

SUMMARY

Disclosed herein are shock wave catheters for intravascular lithotripsy (IVL) and methods of use thereof that do not utilize a guidewire for steering and positioning the shock wave catheter (referred to herein as "guidewireless" shock wave catheters). The guidewireless shock wave catheters disclosed herein can include a core wire that enables the user to steer and position the shock wave catheter. The guidewireless shock wave catheters can be configured to be flexible to allow the catheters to be steered in tortuous regions of vasculature. Flexibility of the shock wave catheters may be enabled by coil(s) or slits along the elongate tube of the shock wave catheter that surrounds the core wire. Because the guidewireless shock wave catheters do not include a lumen for a guidewire, the guidewireless shock wave catheters can have a lower profile than catheters that use a guidewire while still enabling navigation of narrow and tortuous body lumens. In other words, the catheters as disclosed herein can be deployed as a vascular wire, with the additional functionality of delivering IVL therapy.

The guidewireless shock wave catheters include shock wave emitters configured to facilitate flexibility and maneuverability of the catheter. For example, a guidewireless shock wave catheter can include a pair of wires that form a pair of electrodes at their distal tips. The pair of electrodes can be positioned at an opening in a catheter body that enables shock waves to propagate outwardly and/or distally of the catheter. In another example, the guidewireless shock wave catheter includes a shock wave emitter assembly within a distal portion of the catheter that can bend and deflect to maneuver the shock wave catheter through body lumens. The shock wave emitter assembly can include each of a distally emitting shock wave emitter and a laterally emitting shock wave emitter. In another example, the guidewireless shock wave catheter includes a conductive elongate tube and conductive core wire extending within the tube that form a shock wave emitter at the distal end of elongate tube and core wire.

In some examples, a shock wave catheter for treating a lesion of a body lumen is provided, the shock wave catheter comprising: an elongate tube; at least one shock wave emitter disposed distal to the elongate tube and configured to generate at least one shock wave; a distal tip disposed at or proximate to a distal end of the at least one shock wave emitter; and an enclosure enclosing at least the at least one shock wave emitter.

In some examples, a shock wave catheter for treating a lesion of a body lumen is provided, the shock wave catheter comprising: an elongate tube comprising at least one window; a core wire extending within the elongate tube and fixed to a distal end of the elongate tube; at least one shock wave emitter at least partially surrounded by the elongate tube and configured to generate at least one shock wave that propagates through the at least one window; and an enclosure surrounding at least a portion of the elongate tube and enclosing the at least one shock wave emitter.

In some examples, a shock wave catheter for treating a lesion of a body lumen is provided, the shock wave catheter comprising: a shock wave emitter assembly comprising: a first shock wave emitter configured to emit at least one distally directed shock wave; and a second shock wave emitter disposed proximal to the first shock wave emitter, the second shock wave emitter configured to emit at least one laterally directed shock wave; an elongate tube coupled to the shock wave emitter assembly; and an enclosure enclosing the coupled shock wave emitter assembly and elongate tube.

In some examples, a method for treating a lesion of a body lumen is provided, comprising: advancing a shock wave catheter through the body lumen without use of a guidewire such that at least one shock wave emitter enclosed within an enclosure of the shock wave catheter is disposed proximate to the lesion of the body lumen; and generating at least one shock wave by the at least one shock wave emitter to treat the lesion.

In some examples, a system for treating a lesion of a body lumen is provided, comprising: a shock wave catheter comprising: an elongate tube; at least one shock wave emitter disposed distal to the elongate tube and configured to generate at least one shock wave; a core wire extending within the elongate tube and terminating proximate to the shock wave emitter; a distal tip disposed at or proximate to a distal end of the shock wave emitter; and an enclosure enclosing at least the shock wave emitter; and a pulse generator coupled to the at least one shock wave emitter and configured to generate energy pulses to cause the at least one shock wave emitter to generate the at least one shock wave.

In some examples, a system for fluid delivery and removal from a shock wave catheter is provided, comprising: a shock wave catheter comprising: an elongate tube comprising at least one opening to a lumen of the elongate tube at a proximal portion of the elongate tube; a wire extending within the elongate tube and terminating proximate to a distal end of the elongate tube; a shock wave emitter formed by the distal end of the elongate tube and at least a portion of the wire and configured to generate at least one shock wave; and an enclosure enclosing the shock wave emitter and fluidly connected to the lumen of the elongate tube; and a control hub connected to the proximal portion of the elongate tube, the control hub comprising: at least one pressure seal enclosing the at least one opening of the elongate tube; and a fluid port fluidly connected to the at least one opening of the elongate tube, to a vacuum pressure source, and to a conductive fluid source to (a) decrease pressure within at least one of the lumen of the elongate tube and the enclosure, and (b) subsequently draw conductive fluid into at least one of the lumen of the elongate tube and the enclosure.

DESCRIPTION OF THE FIGURES

The invention will now be described, by way of example only, with reference to the accompanying drawings, in which.

DETAILED DESCRIPTION

Figure 1:
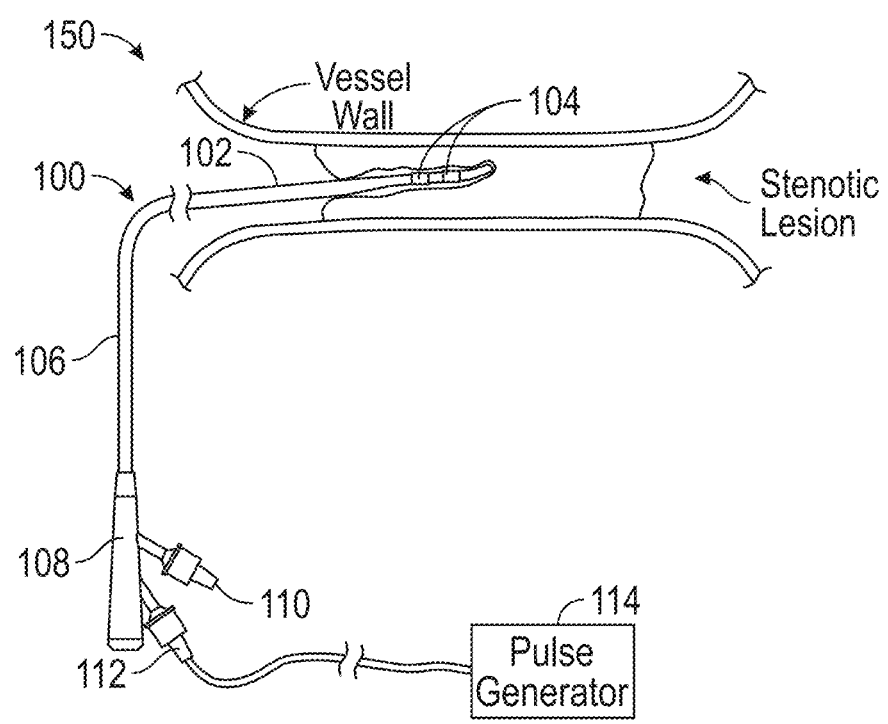
FIG. 1 illustrates an exemplary shock wave catheter system, according to one or more aspects of the present disclosure.

The following description is presented to enable a person of ordinary skill in the art to make and use the various embodiments and aspects thereof disclosed herein. Descriptions of specific devices, assemblies, techniques, and applications are provided only as examples. Various modifications to the examples described herein will be readily apparent to those of ordinary skill in the art, and the general principles described herein may be applied to other examples and applications without departing from the spirit and scope of the various embodiments and aspects thereof. Thus, the various embodiments and aspects thereof are not intended to be limited to the examples described herein and shown but are to be accorded the scope consistent with the claims.

Described herein are shock wave catheters and methods of use thereof that do not utilize a guidewire for steering and positioning the shock wave catheter in a body lumen. In other words, the shock wave catheters described herein are "guidewireless." Guidewireless shock wave catheters can include a core wire for steering and positioning the shock wave catheter rather than sliding the catheter over a guidewire. By eliminating the guidewire lumen, the overall profile of the shock wave catheters can be sufficiently narrow (e.g., similar to that of a guidewire) to enable the guidewireless shock wave catheters to be navigated through tortuous and narrow body lumens. The guidewireless shock wave catheters can be flexible to enable steering of the shock wave catheters through these body lumens. For example, an elongate tube of the shock wave catheter that surrounds the core wire can include one or more coils or slits along the elongate tube of the shock wave catheter.

The guidewireless shock wave catheters described herein achieve a narrow, flexible profile while still including features of shock wave delivery devices that enable shock wave generation and delivery. Thus, the guidewireless shock wave catheters may be utilized to achieve acute luminal gain in heavily occluded lesions (e.g., chronic total occlusions). Moreover, the guidewireless shock wave catheters implement the components for shock wave generation in a manner that facilitates flexibility and maneuverability of the shock wave catheter. For example, the guidewireless shock wave catheter can include a pair of conductive wires extending therein, the ends of which form a shock wave emitter. Shock waves can propagate outward and/or distally from the shock wave emitter of the catheter. In another example, the elongate tube and the core wire of the shock wave catheter themselves can be conductive to form a shock wave emitter at their distal end. In another example, a guidewireless shock wave catheter can include a shock wave emitter assembly within the distal portion of the catheter that can bend and deflect to maneuver the shock wave catheter. The shock wave emitter assembly can include several shock wave emitters, such as a distally emitting shock wave emitter and a laterally emitting shock wave emitter.

Eliminating the use of the guidewire with shock wave catheters can decrease procedure time because it can reduce the number of steps in the procedure. By reducing the number of steps and the overall time spent in a procedure, the risk associated with surgical complications can also be reduced. Using the shock wave catheters described herein can be as simple as advancing the shock wave catheter through a body lumen to position one or more shock wave emitters of the shock wave catheter proximate to a lesion of the body lumen.

As used herein, the term "electrode" refers to an electrically conducting element (typically made of metal) that receives electrical current and subsequently releases the electrical current to another electrically conducting element. In the context of the present disclosure, electrodes are often positioned relative to each other, such as in an arrangement of an inner electrode and an outer electrode. Accordingly, as used herein, the term "electrode pair" refers to two electrodes that are positioned adjacent to each other such that application of a sufficiently high voltage to the electrode pair will cause an electrical current to transmit across the gap (also referred to as a "spark gap") between the two electrodes (e.g., from an inner electrode to an outer electrode, or vice versa, optionally with the electricity passing through a conductive fluid or gas therebetween). More information about the physics of shock wave generation and their control, which can be used for any of the embodiments described herein, can be found in U.S. Pat. Nos. 8,728,091, 9,522,012, and 10,226,265, each of which is incorporated herein by reference in its entirety. In some contexts, one or more electrode pairs may also be referred to as an electrode assembly. In the context of the present disclosure, the term "shock wave emitter" broadly refers to the region of an electrode assembly where the current transmits across the electrode pair, generating a shock wave. The term "emitter band" refers to a continuous or discontinuous band of conductive material that may form one or more electrodes of one or more electrode pairs, thereby forming a location of one or more emitters. One or more of the emitters, emitter bands, and/or electrodes may be formed from a metal, such as stainless steel, copper, tungsten, platinum, palladium, molybdenum, cobalt, chromium, iridium, or an alloy or alloys thereof, such as cobalt-chromium, platinum-chromium, cobalt-chromium-platinum-palladium-iridium, or platinum-iridium, or a mixture of such materials.

Although shock wave catheters described herein generate shock waves based on high voltage applied to electrodes, it should be understood that a shock wave catheter additionally or alternatively may comprise a laser and optical fibers as a shock wave emitter system whereby the laser source delivers energy through an optical fiber and into a fluid to form shock waves and/or vapor bubbles.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof. As provided herein, it should be appreciated that any disclosure of a numerical range describing dimensions or measurements such as thicknesses, length, weight, time, frequency, temperature, voltage, current, angle, etc. is inclusive of any numerical increment or gradient within the ranges set forth relative to the given dimension or measurement.

Guidewireless shock wave catheters can be configured for use with an angioplasty balloon, such as described in U.S. Pat. Nos. 9,730,715 and 10,420,569, each of which are incorporated herein in its entirety. Guidewireless shock wave catheters can be configured to direct shock waves in different directions. For example, forward-biased shock wave catheters, such as that which is described in U.S. Pat. No. 10,966,737 and U.S. Publication No. 2019/0388110, both of which are incorporated herein by reference, direct shock waves in a generally forward direction (e.g., distally from the distal end of a catheter) and can be configured for use without a guidewire, according to the principles described herein. Guidewireless shock wave catheters can be configured to generate shock waves emitted from multiple locations that constructively interfere, such as described in U.S. Publication No. 2023/0123003, incorporated herein by reference in its entirety. Guidewireless shock wave catheters can be configured to deliver several high-voltage pulses in a packet having a short duration (i.e., operable in a "burst mode"), such as described in U.S. patent application Ser. No. 18/595,148, incorporated herein by reference in its entirety. Guidewireless shock wave catheters can be configured to include arrays of low-profile electrode assemblies that reduce the crossing profile of the catheter and allow the catheter to navigate narrow body lumens more easily, such as described in U.S. Pat. Nos. 8,888,788 and 10,709,462 and U.S. Publication No. 2021/0085347, each of which is incorporated herein by reference in its entirety. In some examples, the guidewireless shock wave catheters described herein may be used as a guidewire for other intravascular systems. For example, the guidewireless shock wave catheters may be used as a guidewire for delivering balloon catheters, including but not limited to balloon IVL catheters.

The following description describes exemplary guidewireless shock wave catheters and methods of use thereof with reference to several figures. For example, FIG. 1 is referenced throughout to describe an exemplary shock wave system that does not utilize a guidewire. Exemplary guidewireless shock wave catheters and components thereof are described with respect to FIGS. 2A-2B, 3A-3B, 4, 5, 6, 7A-7E, 8, 9A-9B, 10A-10C, 11, and 12. Exemplary control hubs that facilitate connection of a shock wave catheter with each of a pulse generator and a fluid source are described with respect to FIGS. 13, 14, and 15A-15B. An exemplary method for filling and removing fluid from a shock wave catheter is illustrated in FIG. 16 and described with respect to the diagram in FIGS. 17-17C.

FIG. 1 illustrates an exemplary shock wave system 150 that includes a shock wave catheter 100 being used to treat a stenotic lesion (e.g., an occlusion) in a body lumen (e.g., a vessel). The shock wave catheter 100 is advanced through vasculature to the stenotic lesion without the use of a guidewire. Shock waves can be emitted from one or more shock wave emitters 104 disposed within a distal portion 102 of the shock wave catheter 100 to break up the lesion. The shock wave emitters 104 can be configured to enable flexibility and maneuverability of the shock wave catheter 100 in the body lumen. The shock wave catheter 100 can be filled with a conductive fluid, such as saline. The conductive fluid enables generation of shock waves that propagate from within the distal portion 102 of the shock wave catheter 100 and into the stenotic lesion to open the lesion.

The shock wave catheter 100 can be used to treat lesions of small and/or tortuous body lumens, such as coronary, below-the-knee, etc., arteries and/or other vessels. Accordingly, the shock wave catheter 100 may be sized to enable safe and simple traversal of the catheter through the body lumen. For example, an outer diameter of the shock wave catheter 100 may be no more than about 0.356 mm (i.e., about 0.014 inches). In some examples, the outer diameter of the shock wave catheter 100 may be between about 0.25-1 mm, 0.25-0.75 mm, 0.25-0.5 mm, or 0.25-0.4 mm. This diameter may be applicable at least to the distal portion 102 of the shock wave catheter 100 that is positioned proximate the stenotic lesion. The ability to fit all of the necessary components (e.g., wires, lumen(s), electrodes, etc.) of a functional shock wave emitting device within a catheter of this size is a challenge that heretofore has yet to have been solved.

The shock wave catheter 100 includes a proximal portion 106 that is connected to a control hub 108 (or handle) that remains outside of the patient during a procedure. The control hub 108 includes a fluid port 110 for filling and removing fluid from the shock wave catheter 100. The control hub 108 includes a port 112 that facilitates connection between a pulse generator 114 and the shock wave emitter 104. The pulse generator 114 can be a high voltage source or a laser source. The energy pulses generated by the pulse generator 114 can cause generation of shock waves at the shock wave emitters 104 of the shock wave catheter 100.

To treat a stenotic lesion, the shock wave catheter 100 can be advanced through vasculature to the lesion. The position of the distal portion 102 of the shock wave catheter 100 in the vasculature may be viewed during the procedure in any suitable fashion, including, for example, by using x-ray imaging or fluoroscopy to view at least the distal portion 102 of the shock wave catheter 100. For example, the distal portion 102 of the shock wave catheter 100 (e.g., a distal tip of the shock wave catheter 100) may include a radiopaque marker that is visible under fluoroscopy. The distal portion 102 of the shock wave catheter 100 is then filled with a conductive fluid (e.g., saline) that is introduced via the fluid port 110. After the fluid is introduced, energy pulses from the pulse generator 114 are delivered to the shock wave emitter(s) 104 within the distal portion 102 of the shock wave catheter 100. The energy pulses can be voltage pulses that result in an electrical discharge across a spark gap between electrodes of a given shock wave emitter 104. This discharge generates an acoustic shock wave that propagates outward and through the shock wave catheter 100 to modify the stenotic lesion. In some variations, light energy (e.g., laser energy) is used to generate shock waves. The pulse generator 114 can be a laser source that generates laser pulses that are delivered to the shock wave emitters 104 of the shock wave catheter 100 via one or more optical fibers. Laser pulses emitted from the shock wave emitter(s) 104 can be absorbed by the fluid within the distal portion 102 of the shock wave catheter 100. This absorption process rapidly heats and vaporizes the fluid, thereby generating the rapidly expanding vapor bubble(s), as well as the acoustic shock waves that propagate outward and modify the stenotic lesion. Once the lesion has been sufficiently treated, the shock wave catheter 100 can be withdrawn from the patient.

In some examples, the shock wave catheter 100 described herein can be used to cross a calcified stent that has embedded into a body lumen. A stent previously implanted to a body lumen can become embedded in a body lumen and can cause occlusion of the body lumen. Therefore, the shock wave catheter 100 may be configured to cross such an embedded stent in a body lumen. The shock wave catheter 100 may be advanced through the body lumen to the stent such that the shock wave emitter 104 of the shock wave catheter 100 is disposed proximate to the stent. As described herein, the shock wave catheter 100 may be advanced through the body lumen without the use of a guidewire. Once properly positioned in the body lumen, the shock wave emitter 104 can be configured to generate at least one shock wave, thereby opening the occlusion and enabling the shock wave catheter 100 to cross the embedded stent.

As noted above, the shock wave catheter 100 is advanced through the stenotic lesion without a guidewire. Various features of exemplary shock wave catheters that do not utilize a guidewire are illustrated in and described with respect to FIGS. 2A-2B, 3A-3B, 4, 5, 6, 7A-7E, 8, 9A-9B, 10A-10C, 11, and 12. Unless explicitly stated otherwise, it is to be understood that the features of these shock wave catheters can be incorporated to shock wave catheter 100 in any combination.

Figure 2A:
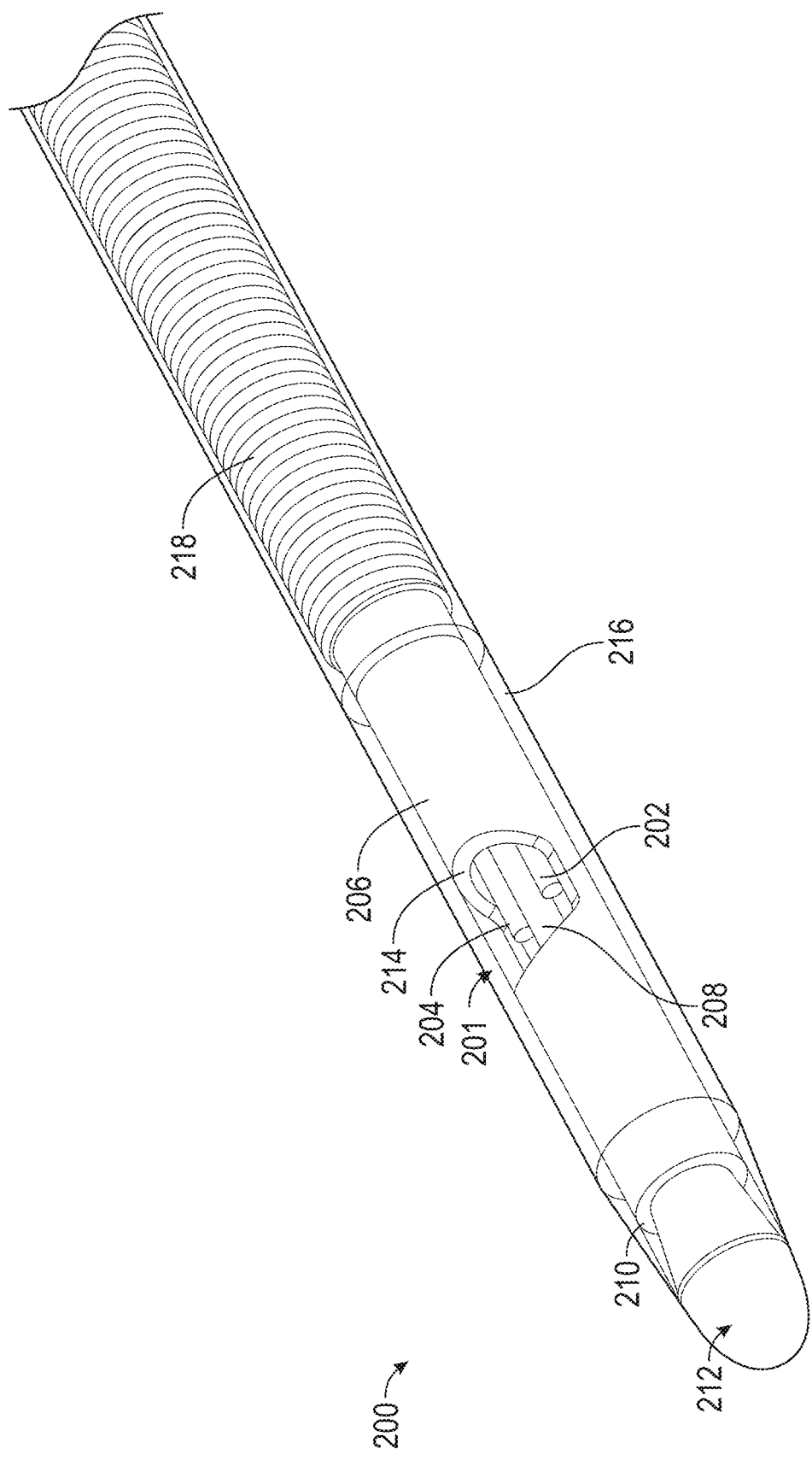
FIG. 2A illustrates a perspective view of a distal portion of an exemplary shock wave catheter that includes a laterally emitting shock wave emitter, according to one or more aspects of the present disclosure.

FIG. 2A illustrates a distal portion of an exemplary shock wave catheter 200 that can be used for shock wave catheter 100. The shock wave catheter 200 includes an elongate tube 206 and a shock wave emitter 201 disposed at a distal region of the elongate tube 206. The shock wave emitter 201 may be formed by a pair of electrodes 202, 204. Each of the electrodes 202, 204 can be electrically connected to a pulse generator, such as by conductive wires extending within the elongate tube 206. In some examples, one or more of the electrodes 202, 204 is provided by the end of a conductive wire. In other words, conductive wires extending along the elongate tube 206 can terminate at a location within the elongate tube 206 and the location where the wires terminate can be the position of the shock wave emitter within the elongate tube 206. This configuration of the electrodes 202, 204 can enable maneuverability and flexibility of the shock wave catheter 200 through narrow body lumens. Although the shock wave catheter 200 includes only a single shock wave emitter 201, it is contemplated that exemplary shock wave catheters described herein can include more than one shock wave emitter, each shock wave emitter formed by an electrode pair. For example, an exemplary shock wave catheter can include 2, 3, 4, etc. shock wave emitters.

The shock wave catheter 200 includes a core wire 208 that extends within the elongate tube 206 and terminates external to the distal end 210 of the elongate tube 206 to form a distal tip 212 of the shock wave catheter 200. The core wire 208 can be a pliable wire that can bend within a desired range of motion, but also can maintain its elongate structure to steer the shock wave catheter 200 through narrow and tortuous body lumens. For example, the core wire 208 may include platinum, platinum-iridium, stainless steel, molybdenum, copper, or a combination thereof. The elongate tube 206 may be made from similar materials as the core wire 208. The elongate tube 206 may include platinum, platinum-iridium, stainless steel, nitinol, titanium, tool steel (i.e., a carbon and alloy steel), or a combination thereof. In some examples, the elongate tube 206 may additionally or alternatively be made from polyimide, polyether block amide (e.g., Pebax®), nylon, polypropylene, polyester, or a combination thereof. Unless explicitly stated otherwise, it is to be understood that the aforementioned materials for each of the elongate tube 206 and the core wire 208 are applicable to any of the other guidewireless shock wave catheter embodiments described herein and having an elongate tube and/or a core wire.

The distal tip 212 formed from the core wire 208 at the distal end 210 of the elongate tube 206 can have a spherical or semi-spherical (e.g., bulbous) geometry that provides a round, soft tip to the shock wave catheter 200 for traversing body lumens without damaging the walls of the lumens. The core wire 208 can be fixed to the distal end 210 of the elongate tube 206 at a surface of the distal tip 212. The bulbous geometry of the distal tip 212 can ease welding of the core wire 208 to the distal end 210 of the elongate tube 206. A diameter of the distal tip 212 extending from the core wire 208 can be greater than the diameter of the elongate portion of the core wire 208 that extends within the elongate tube 206. For example, a diameter of the distal tip 212 may be between about 0.5-1 mm, such as about 0.9 mm, whereas a diameter of the elongate portion of the core wire 208 may be between about 0.05-0.25 mm. The diameter of the distal tip 212 may be substantially the same as the diameter of the overall shock wave catheter 200.

In some examples, the core wire of the shock wave catheter 200 (e.g., core wire 208) may not have a bulbous distal tip. For example, the core wire 208 and the elongate tube 206 may have substantially the same length, both terminating at the distal tip 212 of the shock wave catheter 200. Instead of the distal tip 212 being formed by a bulbous portion extending from the core wire 208, the elongate tube 206 can extend (with the core wire 208) to the distal tip 212 of the shock wave catheter 200 and form the round profile of the distal tip 212. The core wire 208 can be fixed (e.g., welded) to the elongate tube 206 at the distal tip 212. In this example, the elongate tube 206 may include a window (e.g., window 214) for enabling propagation of shock waves from the shock wave emitter 201, described in greater detail below.

The elongate tube 206 includes at least one window 214 in the body of the elongate tube 206 so that shock waves generated by the shock wave emitter 201 can propagate outwardly of the elongate tube 206 through the window 214. The window 214 can be on a side of the elongate tube 206, such that shock waves generated by the shock wave emitter propagate outward in a lateral direction from the shock wave catheter 200. The window 214 can be formed by a cut-out (or opening) in the body of the elongate tube 206. In some examples, the window 214 can include a material that is transparent or semi-transparent to shock waves. The window 214 may extend between about 10-90% of the circumference of the elongate tube 206. For example, the window 214 may extend between about 20-80%, 30-70%, or 40-60% of the circumference of the elongate tube 206. The degree to which the window 214 extends along the circumference of the elongate tube 206 can influence the direction that the shock waves generated by the shock wave emitter can propagate outward from the shock wave catheter 200.

The shock wave catheter 200 includes an enclosure 216 that surrounds at least a portion of the elongate tube 206, and in particular, at least the portion of the elongate tube 206 having the window 214. The enclosure 216 can include a material that permits passage of shock waves into the body lumen. For example, the enclosure 216 can include Teflon, polyether block amide (PEBA, e.g., Pebax®), polytetrafluoroethylene (PTFE), nylon, polyurethane (e.g., Texin®, Tecothane™), polycarbonate, polyether ether ketone (PEEK), or another polymer. The material of the enclosure 216 may be a thermoset or thermoplastic material. Unless explicitly stated otherwise, it is to be understood that the materials described herein with respect to enclosure 216 are applicable to enclosures of other guidewireless shock wave catheter embodiments described herein. The enclosure 216 may extend over 20%, 40%, 60%, 80%, 90%, or substantially all of the length of the elongate tube 206. In some examples, the enclosure 216 surrounds the distal portion of the elongate tube 206, and the remainder of the elongate tube 206 is coated (e.g., with Teflon or another hydrophilic coating). In some examples, the elongate tube 206 is coated with an electrically insulating coating (e.g., polyimide, TPU, etc.). The enclosure 216 may be sealed to the elongate tube 206 to maintain a closed system within the shock wave catheter 200 to contain fluid, such as conductive fluid, within the enclosure 216.

Figure 2B:
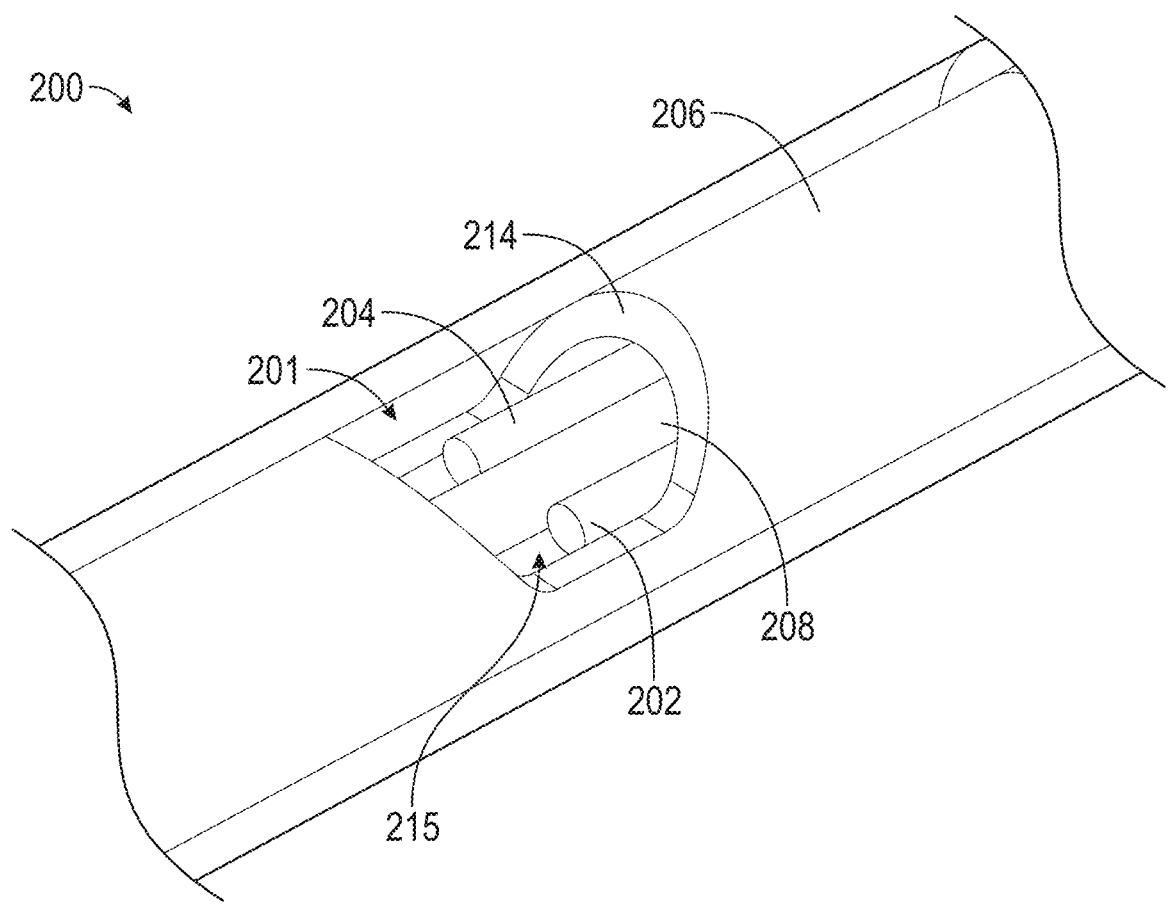
FIG. 2B illustrates an enlarged view of the laterally emitting shock wave emitter of FIG. 2A, according to one or more aspects of the present disclosure.

The enclosure 216 can be filled with a fluid using the innate lumen 215 of the elongate tube 206 (depicted in FIG. 2B). For example, the enclosure 216 can be filled with a conductive fluid that facilitates generation and propagation of the shock waves generated by the shock wave emitter 201 within the enclosure 216 and outward into the body lumen. When filled, the enclosure 216 may expand within a predetermined limit. Alternatively, the enclosure 216 may not expand when it is filled. In either instance, the overall diameter of the shock wave catheter 200 may remain under about 1 mm, such as under about 0.9 mm (e.g., about 0.035 inches).

The elongate tube 206 can include a coil 218 that allows at least a portion of the elongate tube 206 to bend and turn through tortuous vessels. The coil 218 can be attached (e.g., welded) to the remainder of the elongate tube 206. The pitch of the coil 218 may be constant or variable throughout the length of the coil 218. For example, the pitch of the coil 218 may be between about 0.005-0.120 mm, such as about 0.005-0.015 mm, 0.015-0.05 mm, or 0.05-0.12 mm. In some examples, the elongate tube 206 can include slits that are cut (e.g., laser-cut) into the elongate tube 206 and enable flexibility of the elongate tube 206. The coil 218 (and/or slits) can extend along about 20-80% of the length of the elongate tube 206. As illustrated in FIG. 2A, the coil 218 may terminate at a portion of the elongate tube 206 prior to the window 214 on the tube. The remainder of the elongate tube 206 distal to the coil 218 may be rigid. By maintaining rigidity in the distal portion of the shock wave catheter 200, the distal end of the shock wave catheter 200 can easily guide the catheter through occlusions, including through soft thrombi and occlusions that may be stiff. Also, the rigidity of the distal portion of the elongate tube 206 could allow the physician to control directionality of the shock waves generated within the distal portion of the shock wave catheter 200 and in turn ensure accurate and efficacious IVL therapy.

Figure 3A:
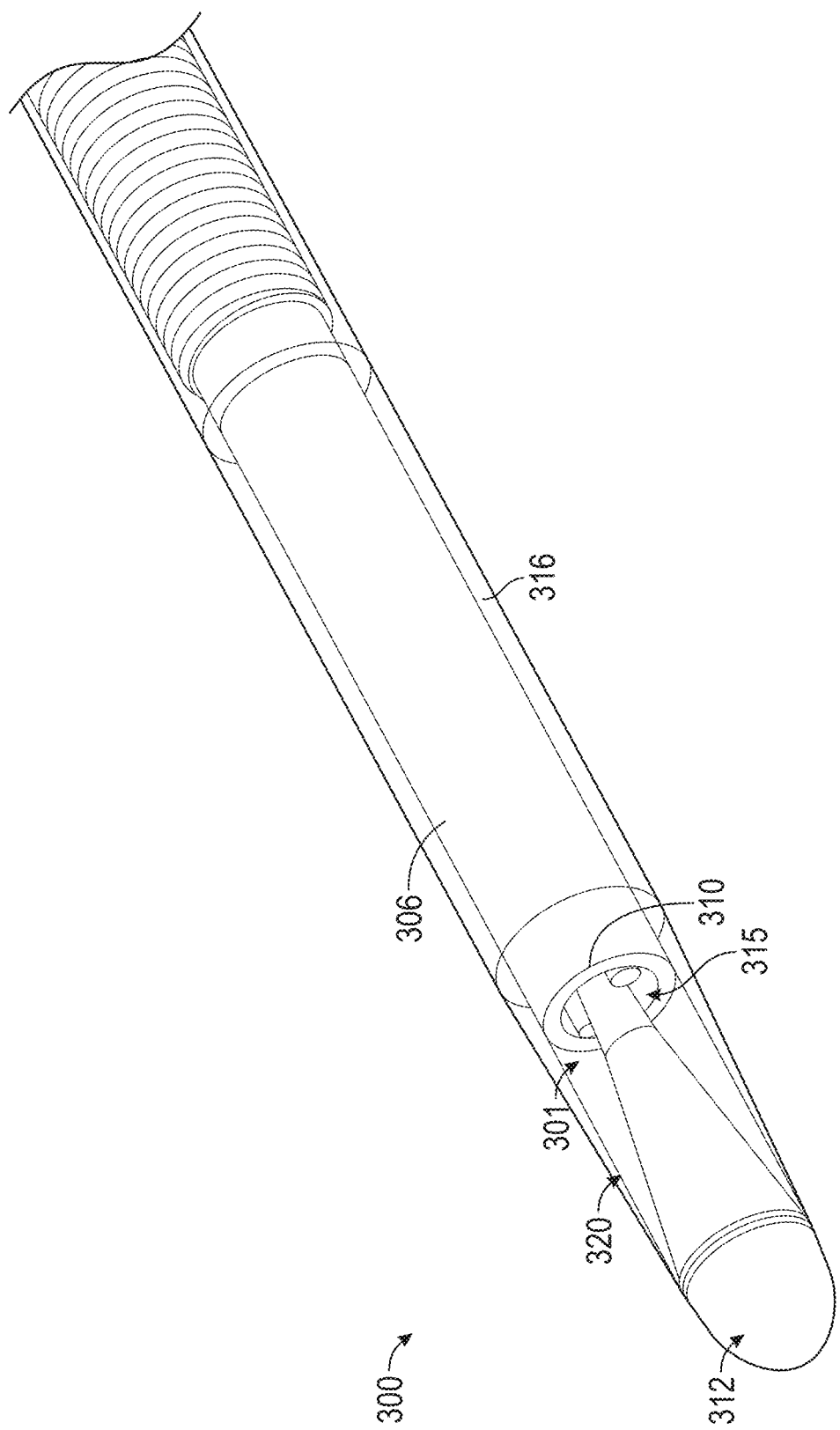
FIG. 3A illustrates a perspective view of a distal portion of an exemplary shock wave catheter that includes a shock wave emitter at a distal end of an elongate tube of the shock wave catheter, according to one or more aspects of the present disclosure.
Figure 3B:
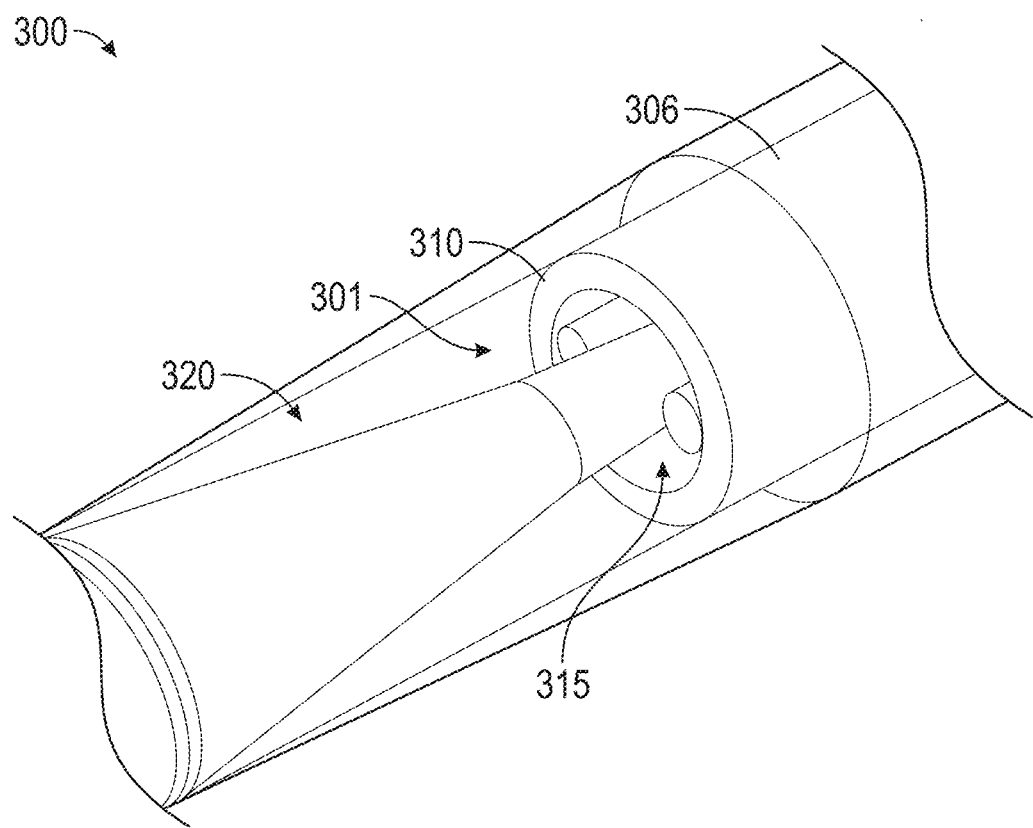
FIG. 3B illustrates an enlarged view of the shock wave emitter of FIG. 3A, according to one or more aspects of the present disclosure.

FIGS. 3A-3B illustrate an exemplary shock wave catheter 300 that includes similar features to shock wave catheter 200 and also can be used for shock wave catheter 100 in shock wave system 150. The shock wave catheter 300 differs from shock wave catheter 200 in that it is configured to emit shock waves from the distal end 310 of the elongate tube 306 of the shock wave catheter 300 as opposed to from a window in the side of the elongate tube. The distal end 310 of the elongate tube 306 can be spaced apart from the distal tip 312 of the shock wave catheter 300 (e.g., by a space 320) to enable the shock waves to propagate radially and/or distally outward from the shock wave catheter 300.

The enclosure 316 surrounds a portion of the distal tip 312 and at least a portion of the distal end 310 of the elongate tube 306. The enclosure 316 is sealed to the elongate tube 306 to create a closed system at the distal portion of the shock wave catheter 300. The lumen 315 of the elongate tube 306 can deliver a conductive fluid to the space 320 within the enclosure 316. As noted above, the conductive fluid can enable generation and propagation of shock waves by the shock wave emitter 301. The enclosure 316 may be taut against the distal tip 312 and the elongate tube 306 to maintain a stable, secure connection between the distal tip 312 and the distal portion of the elongate tube 306.

Figure 4:
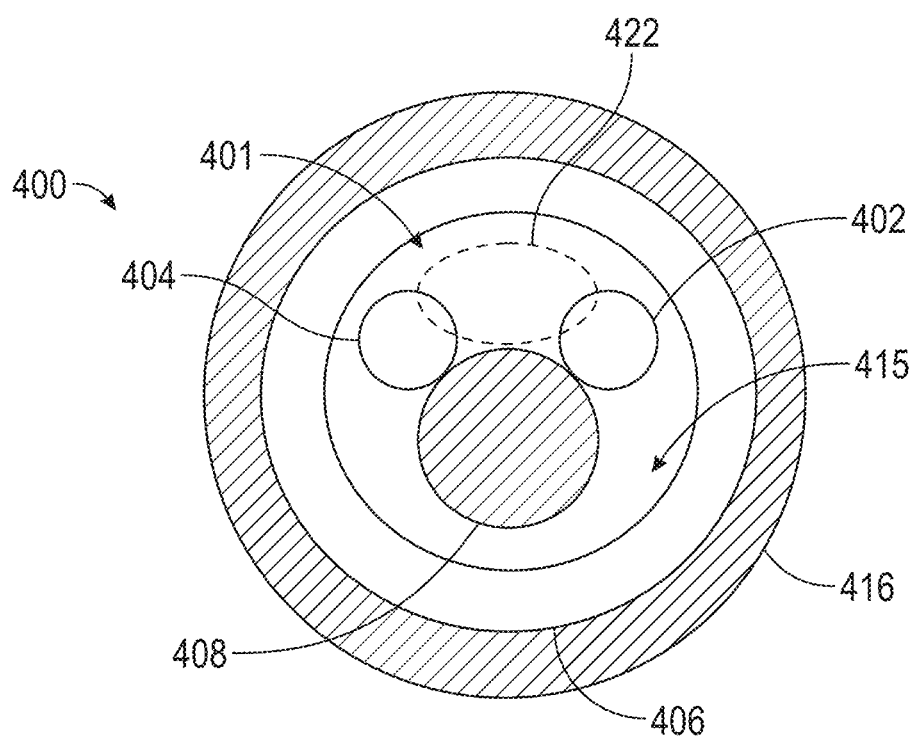
FIG. 4 illustrates a cross-sectional view of an exemplary shock wave catheter that includes a shock wave emitter, according to one or more aspects of the present disclosure.

FIG. 4 is a cross-sectional view of an exemplary shock wave catheter 400. The cross-sectional view of the shock wave catheter 400 can represent a cross-sectional view of the shock wave catheter 300 (e.g., at the distal end 310 of the elongate tube 306). The shock wave catheter 400 can individually be understood to represent a cross-sectional view of the shock wave catheter 200 (e.g., at the window 214 in the body of the elongate tube 206).

Shock wave emitter 401 can include a pair of wires extending within a lumen 415 of an elongate tube 406, the distal ends of which form electrodes 402, 404. The pair of wires may extend along core wire 408. Electrodes 402, 404 are positioned at the distal end of the elongate tube 406 and are separated by a spark gap 422. When a suitably high voltage pulse can be is applied across the pair of electrodes 402, 404, current can flow across the spark gap 422 between the electrodes 402, 404 through a conductive fluid contained within the enclosure 416. The current flow generates a spark that creates one or more shock waves. Delivering a series of energy pulses to the shock wave emitter 401 can generate a series of shock waves.

Figure 5:
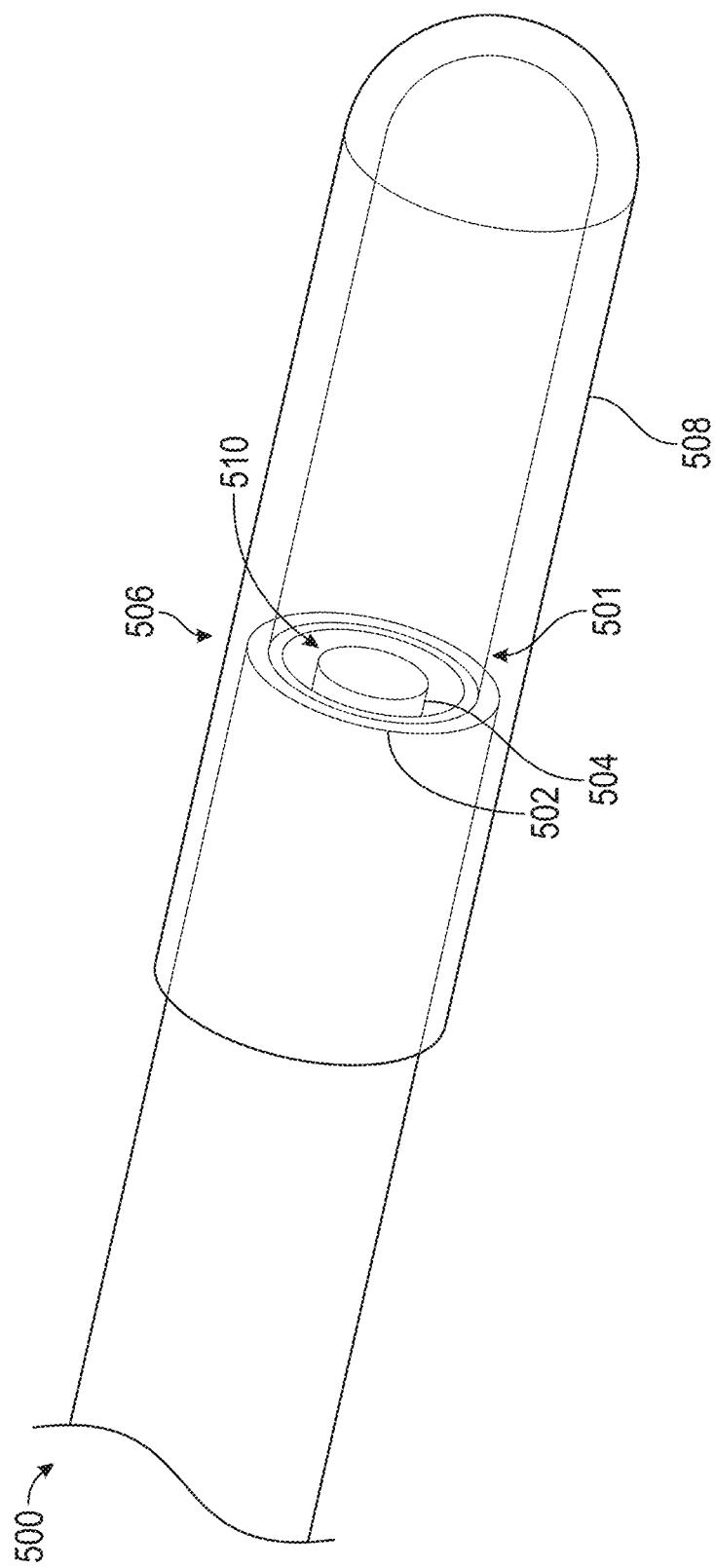
FIG. 5 illustrates a perspective view of a distal portion of an exemplary shock wave catheter that includes a conductive core wire disposed within a conductive elongate tube, according to one or more aspects of the present disclosure.

FIG. 5 illustrates another exemplary shock wave catheter 500 that can be used for shock wave catheter 100 in shock wave system 150 and thus does not use a guidewire. The shock wave catheter 500 includes an elongate tube 502 and a core wire 504 extending within the elongate tube 502 and terminating proximate to the distal end of the elongate tube 502. Each of the elongate tube 502 and the core wire 504 are conductive. The ends of the elongate tube 502 and the core wire 504 can form a shock wave emitter 501. Thus, when a suitably high voltage pulse is applied to the shock wave emitter 501, a shock wave can be generated at the distal end 506 of the elongate tube 502 and core wire 504. The configuration of the shock wave emitter 501 formed by the elongate tube 502 and core wire 504 can contribute to the narrow profile of the shock wave catheter 500, as well as the maneuverability and flexibility of the shock wave catheter 500.

Each of the elongate tube 502 and the core wire 504 can include one or more materials described herein with respect to alternative embodiments of guidewireless shock wave catheters (e.g., shock wave catheter 200). For example, the elongate tube 502 can include nitinol (NiTi). The core wire 504 can include a distal tip made of a material with a high melting point (i.e., greater than 1500 degrees Celsius). In some embodiments, the core wire 504 may include a copper wire along portions of the core wire 504 and a distal end made of molybdenum. At least a portion of the elongate tube 502 (e.g., the inner surface and/or outer surface of the elongate tube 502) can be coated (e.g., dip coated) with an insulating coating (e.g., Teflon) to prevent premature release of the electricity traveling along the elongate tube 502. The core wire 504 can additionally or alternatively be coated.

The shock wave catheter 500 can include an enclosure 508 that encloses at least the distal end 506 of the elongate tube 502 and core wire 504 (i.e., the shock wave emitter 501). The enclosure 508 can be sealed to a distal portion of the elongate tube 502 and extend beyond the distal end 506 of the elongate tube 502 and the core wire 504. The portion of the elongate tube 502 (e.g., a proximal portion of the elongate tube 502) that is not covered by the enclosure 508 may be coated, as noted above, with an insulating coating to prevent electricity from prematurely releasing from the elongate tube 502 and damaging the body lumen.

The lumen 510 of the elongate tube 502 can deliver fluid to fill the enclosure 508. Filling the enclosure 508 can include pressurizing the enclosure 508, for example, to a pressure of about 1-6 atm. The shape (e.g., diameter) of the enclosure 508 may not change substantially between an unfilled and a filled state of the enclosure 508. Alternatively, the enclosure 508 can be expandable to accommodate filling the enclosure 508. The enclosure 508 may expand within a predetermined limit to maintain the narrow profile of the shock wave catheter 500. For example, a diameter of the enclosure 508 when it is in its filled state may be no more than about 4 mm. Expanding the enclosure 508 can connote that the material of the enclosure 508 undergoes elastic stretching when it is filled, but it is not intended to be limited to this definition. The enclosure 508 may expand from the unfilled state to the filled state, and the material of the enclosure 508 may not stretch at all. When the enclosure 508 is filled and energy is applied at the shock wave emitter 501, shock waves can be generated at the spark gap between the distal end 506 of the elongate tube 502 and the core wire 504 that propagate distally outward through the enclosure 508 and outside of the shock wave catheter 500 to the body lumen.

Figure 6:
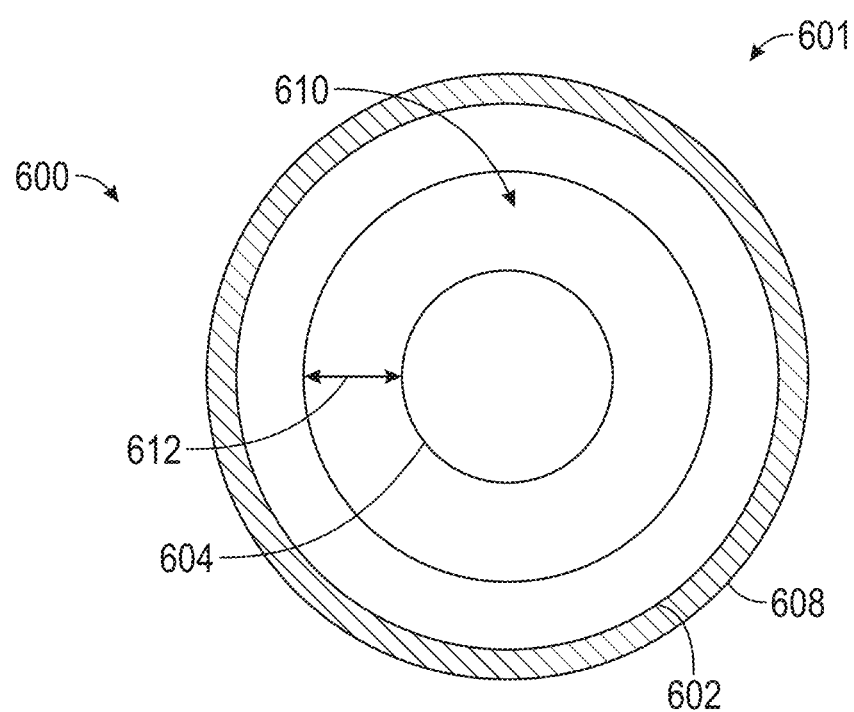
FIG. 6 illustrates a cross-sectional view of an exemplary shock wave catheter that includes a conductive core wire disposed within a conductive elongate tube, according to one or more aspects of the present disclosure.
Figure 7A:
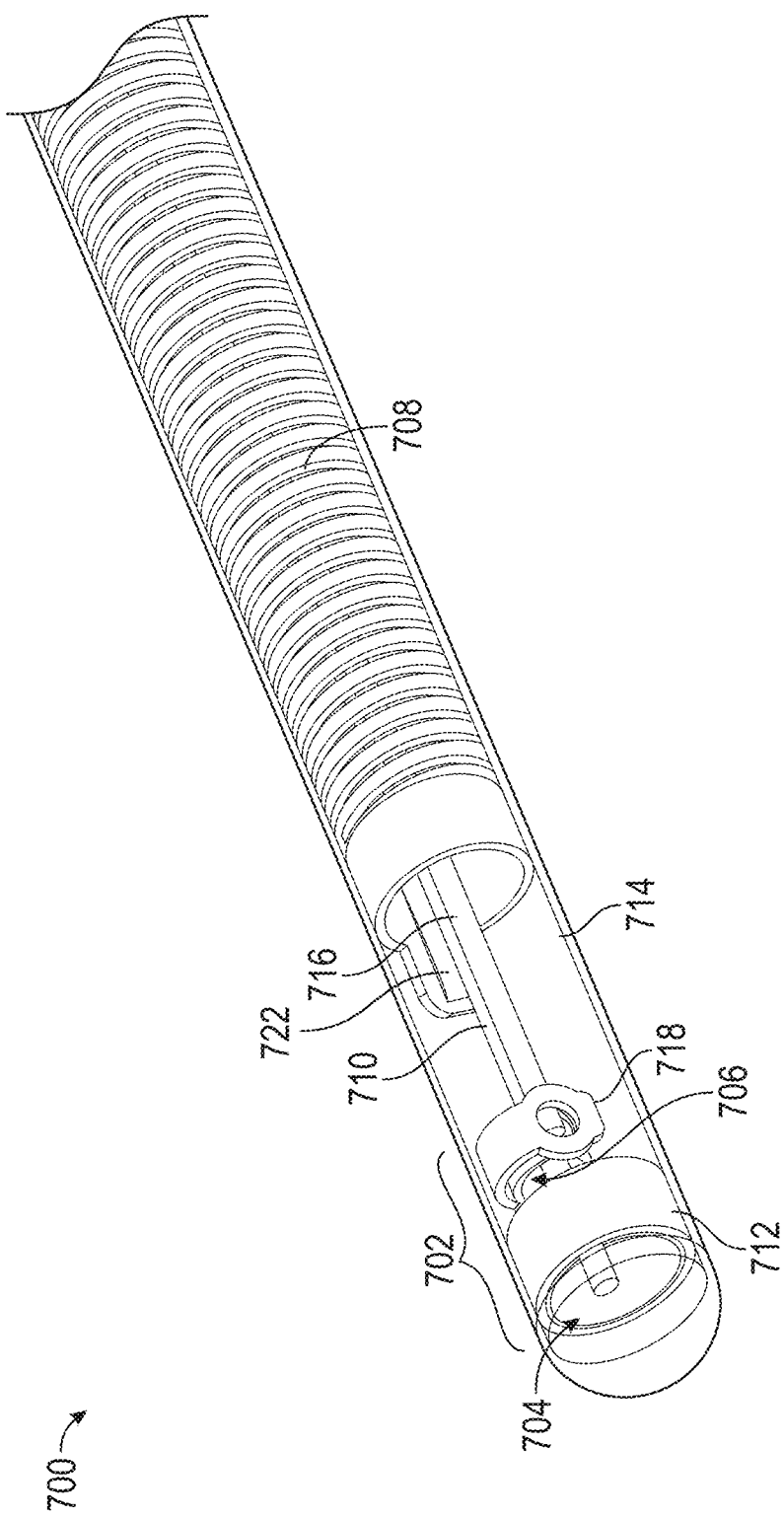
FIG. 7A illustrates a perspective view of a distal portion of an exemplary shock wave catheter that includes a shock wave emitter assembly including a laterally emitting shock wave emitter and a distally emitting shock wave emitter, according to one or more aspects of the present disclosure.
Figure 7B:
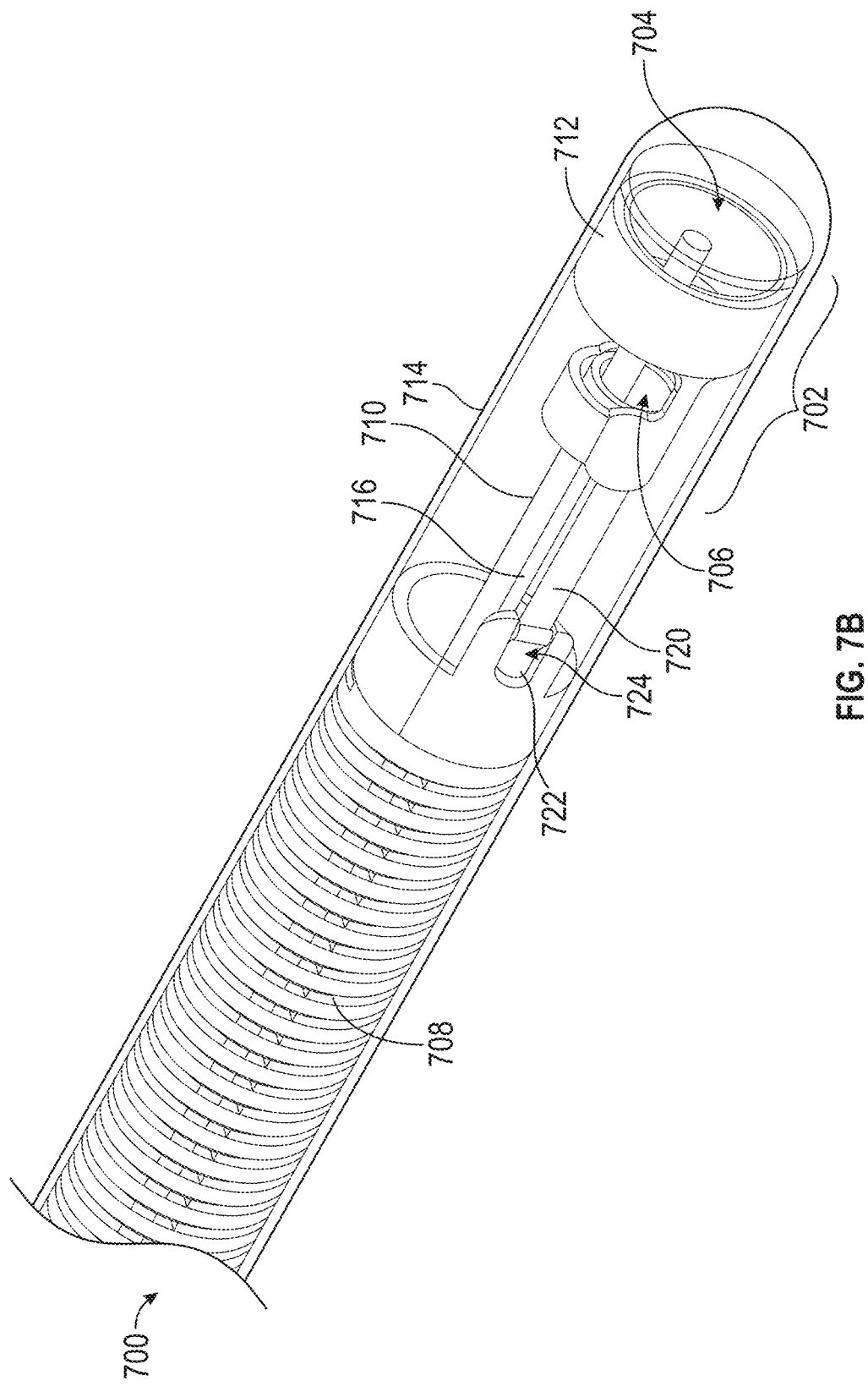
FIG. 7B illustrates another perspective view of the distal portion of the exemplary shock wave catheter including a shock wave emitter assembly, according to one or more aspects of the present disclosure.
Figure 7C:
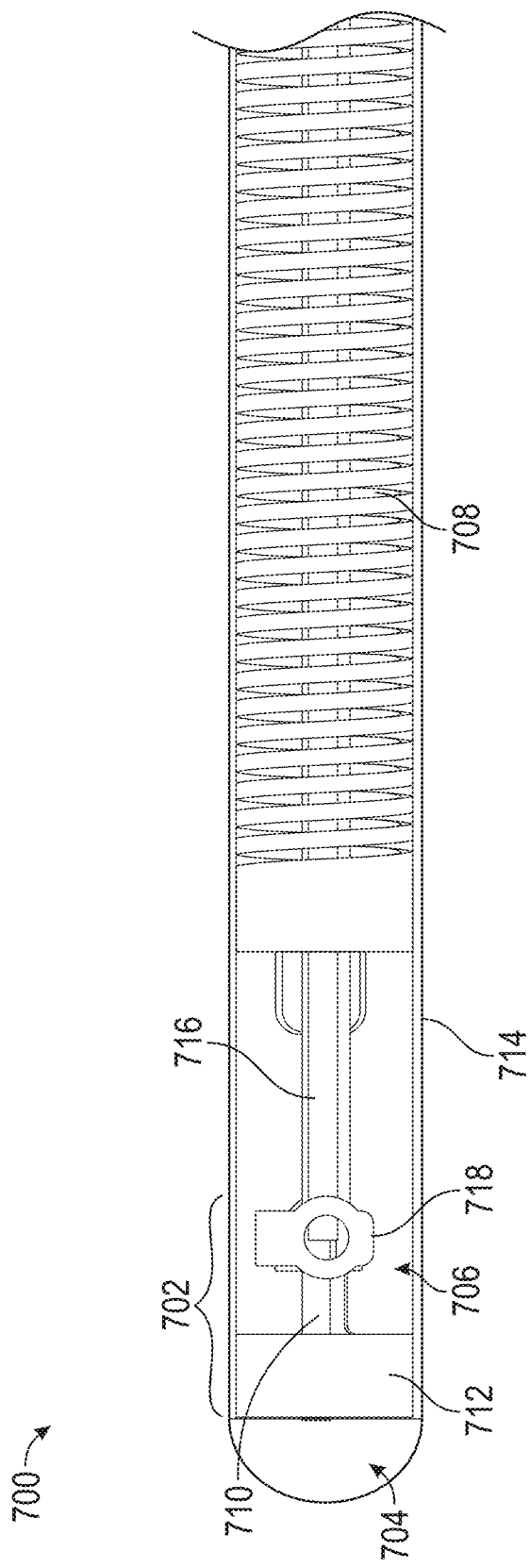
FIG. 7C illustrates a side view of the distal portion of the exemplary shock wave catheter including a shock wave emitter assembly, according to one or more aspects of the present disclosure.
Figure 7D:
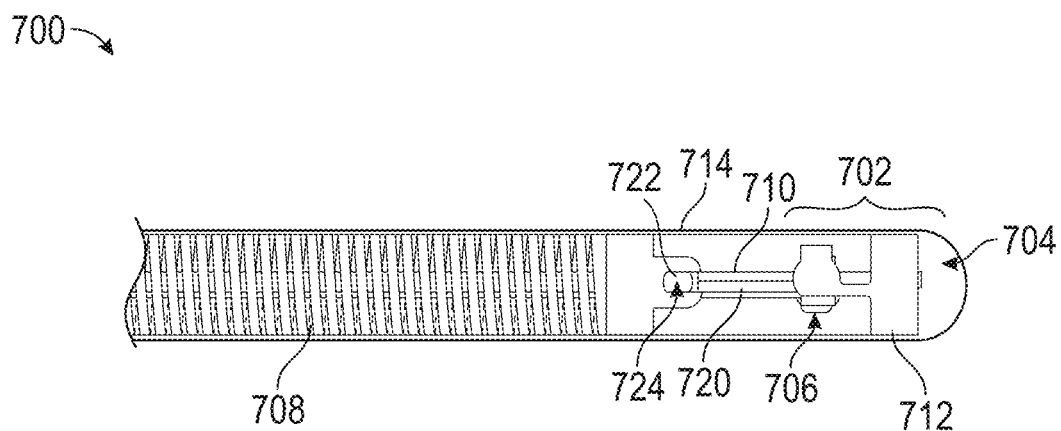
FIG. 7D illustrates another side view of the distal portion of the exemplary shock wave catheter including a shock wave emitter assembly, according to one or more aspects of the present disclosure.
Figure 7E:
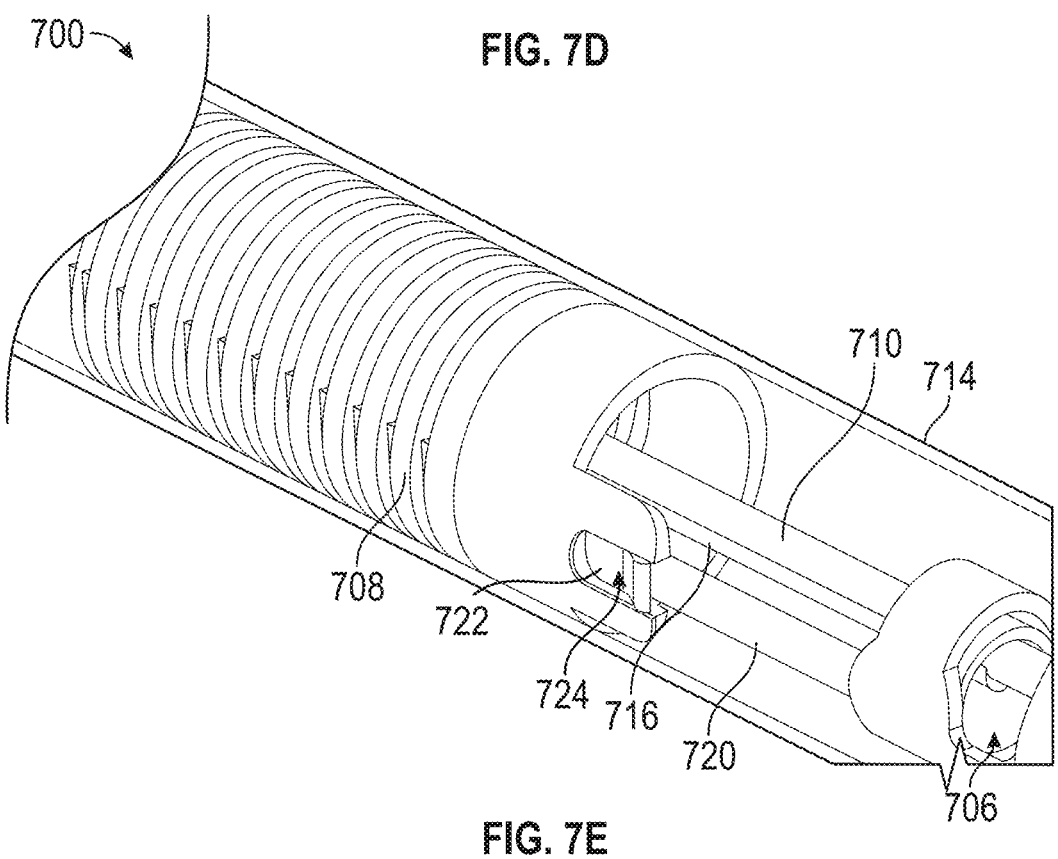
FIG. 7E illustrates a detailed view of a mechanism connecting the shock wave emitter assembly to an elongate tube of the exemplary shock wave catheter, according to one or more aspects of the present disclosure.

FIG. 6 illustrates a cross-section of a distal end of an exemplary shock wave catheter 600 that can represent the distal end 506 of the shock wave catheter 500. FIG. 6 can be used to demonstrate the gap 612 between the distal end 606 of the conductive elongate tube 602 and the core wire 604 (i.e., the shock wave emitter 601), in which shock waves can be generated. As noted above, the lumen 610 of the elongate tube 602 (which encompasses the gap 612) can fill the enclosure 608 with fluid to enable shock wave generation at the gap 612 that propagate outward. An inner diameter of the elongate tube 602 may be between about 0.1-0.4 mm. A diameter of the core wire 604 may be between about 0.05-0.25 mm. A length of the gap 612 can be defined as half the difference between the inner diameter of the elongate tube 602 and the diameter of the core wire 604. For example, the length of the gap 612 may be between about 0.001-0.2 mm.

FIGS. 7A-7E illustrate another exemplary shock wave catheter 700 that is used without a guidewire and can be used for the shock wave catheter 100 in shock wave system 150. The shock wave catheter 700 includes a shock wave emitter assembly 702 having multiple shock wave emitters that can emit multiple shock waves in the same or in different directions. The shock wave emitter assembly 702 includes a shock wave emitter 704 that can emit distally directed shock waves and a shock wave emitter 706 that can emit laterally (e.g., radially outward) directed shock waves. The shock wave emitter assembly 702 can be configured within the shock wave catheter 700 such that it can bend and deflect as the shock wave catheter 700 is advanced through body lumens, thus enabling flexibility and maneuverability of the shock wave catheter 700.

Each of the shock wave emitters 704, 706 of the shock wave emitter assembly 702 may be coupled to a pulse generator that delivers energy to the shock wave emitters 704, 706. The shock wave catheter 700 includes a conductive wire 710 that extends through the elongate tube 708 and terminates at the distally emitting shock wave emitter 704 to apply energy across the shock wave emitter 704. The distal end of the conductive wire 710 can form an electrode of an electrode pair of the shock wave emitter 704. The shock wave emitter assembly 702 can include an emitter band 712 that forms the other electrode (e.g., the return electrode) of the electrode pair of the shock wave emitter 704. The emitter band 712 can be a conductive material that has an annular or semi-annular shape. In the shock wave catheter 700, the emitter band 712 is an annular band of conductive material that extends along the circumference of the enclosure 714. When voltage is applied across the shock wave emitter 704 by the conductive wire 710, current can flow from the end of the conductive wire 710 to the emitter band 712, causing a distally directed shock wave to be generated by the shock wave emitter 704.

The shock wave catheter 700 also includes a conductive wire 720 that applies energy across the shock wave emitter 706. The conductive wire 720 extends through the elongate tube 708 and terminates at the laterally emitting shock wave emitter 706. One electrode of an electrode pair of the shock wave emitter 706 can be formed by the distal end of the conductive wire 720, and the other electrode (e.g., the return electrode) of the electrode pair of the shock wave emitter 706 can be formed by an emitter band 718 of the shock wave emitter assembly 702. The emitter band 718, like emitter band 712, can be a conductive material having an annular or semi-annular shape. In the shock wave catheter 700, the emitter band 718 has a semi-annular shape that terminates with an annular (or ring-shaped) electrode that is positioned at the side of the shock wave catheter 700. When voltage is applied across the shock wave emitter 706 by the conductive wire 720, current can flow from the end of the conductive wire 720 to the emitter band 718, causing a laterally directed shock wave to be generated by the shock wave emitter 706.

The shock wave emitters 704, 706 may be individually coupled to the pulse generator to enable energy to be delivered to the emitters separately, in turn causing the emitters to emit separate shock waves. In this example, the conductive wires 710, 720 can be individually connected to the pulse generator. Alternatively, the shock wave emitters 704, 706 may be coupled to one another, such that energy applied across the shock wave emitters 704, 706 causes the emitters to emit shock waves simultaneously or near-simultaneously. In this example, the conductive wires 710, 720 can be connected to each other (e.g., at or near the pulse generator).

Each of the shock wave emitters 704, 706 can be coupled to a conductive wire 716 that extends through the shock wave catheter 700 and is coupled to a pulse generator to complete the electrical circuit. In this manner, the shock wave emitters 704, 706 can be grounded to the pulse generator by the conductive wire 716. In some examples, the shock wave catheter 700 can include more than one conductive wire similar to conductive wire 716 for grounding each of the shock wave emitters 704, 706.

The shock wave emitter assembly 702 is coupled to the elongate tube 708 by a core wire 722. The core wire 722 can extend through the elongate tube 708 and can terminate at the distal portion of the shock wave catheter 700 proximate to the distal end of the elongate tube 708. At its proximal end, the core wire 722 can be coupled to a control hub (described in greater detail below) to control bending and deflection of the distal tip of the shock wave catheter 700 that contains the shock wave emitter assembly 702. In some examples, the distal end of the elongate tube 708 can be welded to the core wire 722 (e.g., at junction 724) to enable tip deflection of the shock wave catheter 700. In some examples, (e.g., in place of or in addition to conductive wire 716) the core wire 722 may be conductive, such that energy received at the return electrodes formed by the shock wave emitter assembly 702 can travel through the core wire 720 to the control hub.

The elongate tube 708 and the shock wave emitter assembly 702 are enclosed (e.g., surrounded) by an enclosure 714. The enclosure 714 can be fillable, for example, with a conductive fluid that is delivered to the distal portion of the shock wave catheter 700 by the lumen of the elongate tube 708. The enclosure 714 can be closed at the distal end of the shock wave catheter 700 to create a closed system for the conductive fluid delivered to the distal portion of the shock wave catheter 700. The enclosure 714 can include a thermoplastic, thermoset, or other polymer material that conforms to the elongate tube 708 and the shock wave emitter assembly 702. In some examples, when fluid is delivered through the lumen of the elongate tube 708 to the portion of the enclosure 714 around the shock wave emitter assembly 702, the enclosure 714 may not noticeably expand, so as to maintain the narrow profile of the shock wave catheter 700.

Figure 8:
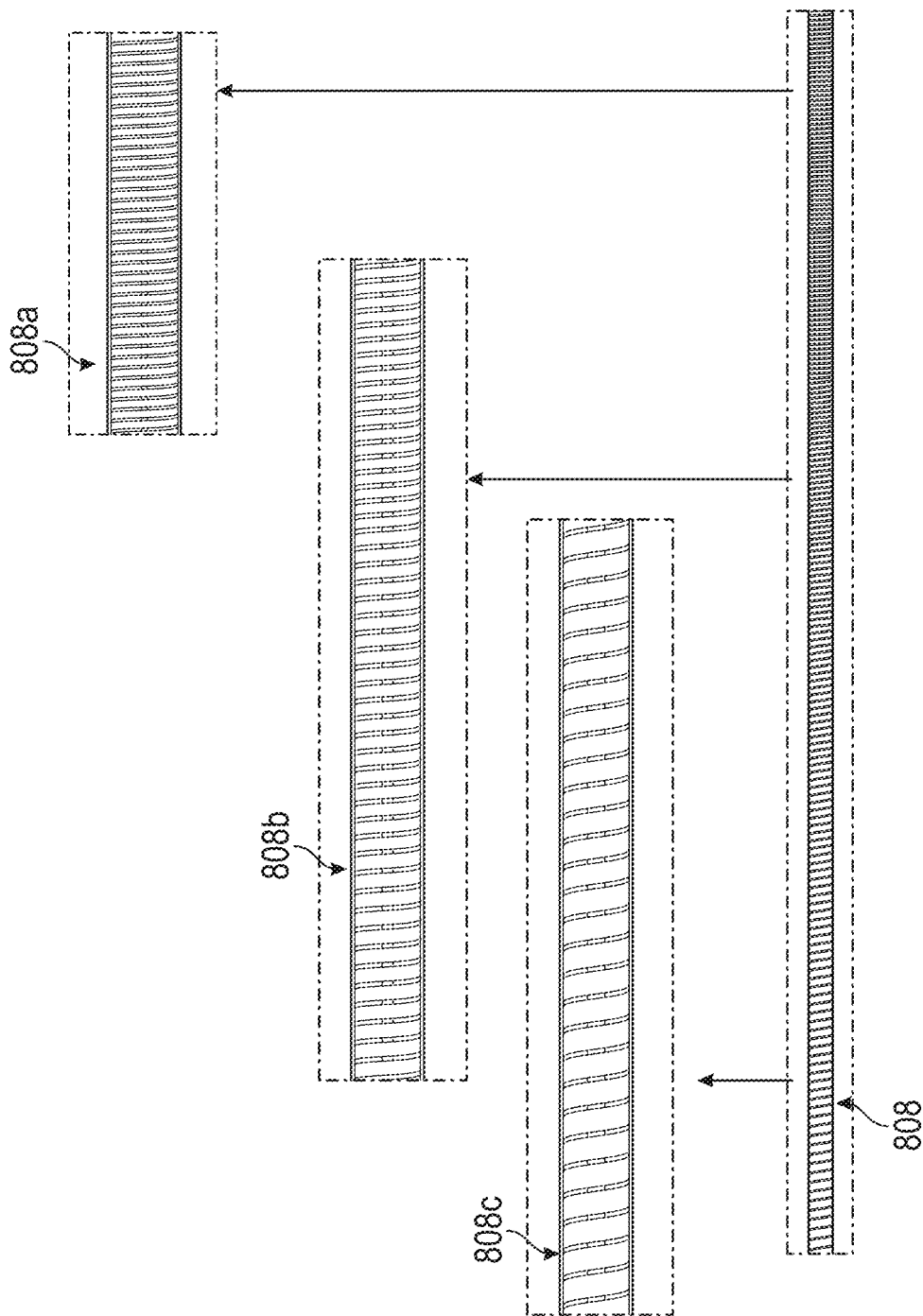
FIG. 8 illustrates a side view of an elongate tube of an exemplary shock wave catheter with enlarged views of different portions of the elongate tube, according to one or more aspects of the present disclosure.

The elongate tube 708 can include a coil and/or slits cut into the elongate tube 708 that enable flexibility of the elongate tube 708. For example, the elongate tube 708 can include a flat wire coil that has a consistent or variable pitch along the length of the elongate tube 708. FIG. 8 illustrates an elongate tube 808 that can be used for the elongate tube 708. The elongate tube 808 includes a coil having a variable pitch that can enable flexibility of the shock wave catheter at the distal portion 808c of the tube, but then stiffens at the proximal portion 808a of the tube (e.g., where it is connected to the control hub). Thus, the pitch of the elongate tube 808 increases from the proximal portion 808a, to the middle portion 808b, to the distal portion 808c of the elongate tube 808. In some embodiments, the pitch of the helical coil at the distal portion 808c is at least two times greater than the pitch at the proximal portion 808a. The pitch of the middle portion 808b located between the distal portion 808c and the proximal portion 808a can be less than the pitch at the distal portion 808c, and greater than the pitch at the proximal portion 808a. In some embodiments, the proximal portion 808a of the elongate tube 808 includes a coil that extends proximally to an uncoiled portion (i.e., where it is connected to the control hub).

In some embodiments, the distal portion 808c of the elongate tube 808 has a malleability similar to that of a similarly sized conventional guidewire (e.g., a 0.035", or about 0.9 mm, thick guidewire). In use, such embodiments may advantageously allow physicians to bend and shape the distal portion 808c of the elongate tube 808 in a manner similar to how they would bend and shape conventional guidewires to access target anatomy (e.g., neurovasculature or the vasculature below the knee). In some embodiments, the distal portion of the elongate tube 808 may include a bent region having a bend up to 90 degrees. In some embodiments, the distal portion of the elongate tube 808 may include a hook or a U-shaped region.

Figure 9A:
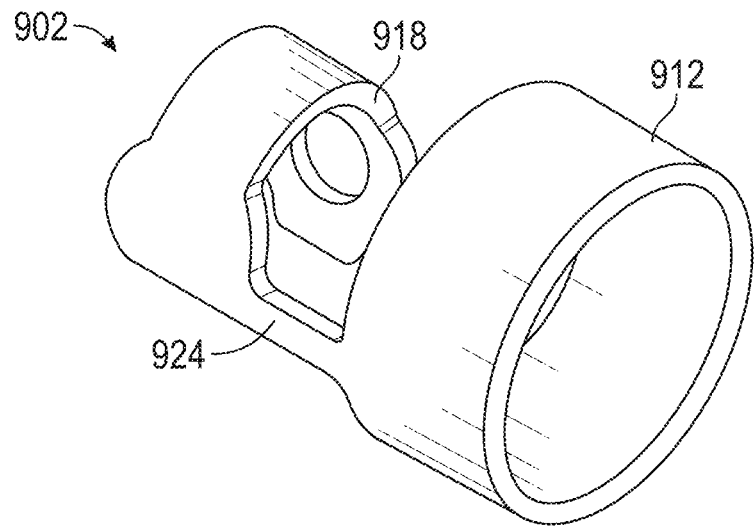
FIG. 9A illustrates a perspective view of a shock wave emitter assembly of an exemplary shock wave catheter, according to one or more aspects of the present disclosure.
Figure 9B:
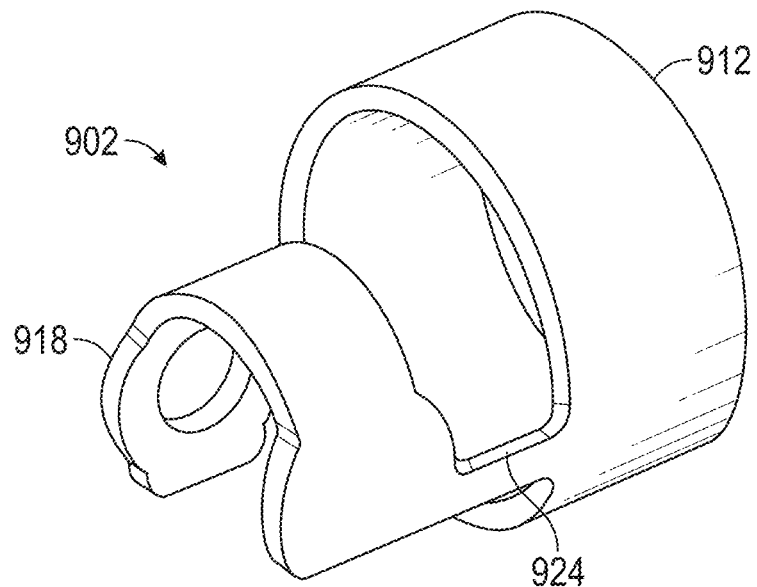
FIG. 9B illustrates another perspective view of the shock wave emitter assembly of an exemplary shock wave catheter, according to one or more aspects of the present disclosure.

FIGS. 9A-9B illustrate a shock wave emitter assembly 902 that can be used for shock wave emitter assembly 702 of shock wave catheter 700. As noted above, the shock wave emitter assembly 702 can form return electrodes of a distally emitting shock wave emitter and a laterally emitting shock wave emitter that may be in the form of emitter bands. With reference to FIGS. 9A-9B, the emitter band 912 can form the return electrode of a distally emitting shock wave emitter, and the emitter band 918 can form the return electrode of a laterally emitting shock wave emitter. The emitter band 912 can be positioned proximal to the emitter band 918 when the shock wave emitter assembly 902 is disposed in a shock wave catheter. The emitter bands 912, 918 can be attached by an attachment portion 924 of the shock wave emitter assembly 902. The length of the attachment portion 924 may vary based on the desired profile of the shock waves emitted by the shock wave emitter assembly 902. The length of the attachment portion 924 (i.e., a distance between the emitter bands 912, 918) may be limited such that the flexibility of the shock wave emitter assembly 902 is not adversely affected. Stated another way, a shorter length of the attachment portion 924 may be preferable to a longer length of an attachment portion 924 to prevent the shock wave emitter assembly 902 from being overly flexible.

The emitter bands 912, 918 of the shock wave emitter assembly 902 can be sized to fit into a narrow guidewireless shock wave catheter. For example, an outer diameter of the emitter bands 912, 918 may be between about 0.25-2 mm, such as between about 0.5-1.5 mm. One or more of the emitter bands 912, 918 may be a discontinuous emitter band that enables the shock wave emitter assembly 902 to be used in shock wave catheters of various sizes. In the shock wave emitter assembly 902, the emitter band 912 extends from the attachment portion 924 in an annular shape that can mimic the circular profile of a shock wave catheter. The emitter band 918 extends from the attachment portion 924 in a semi-annular shape that partially mimics the circular profile of a shock wave catheter but terminates at the side of the shock wave emitter assembly 902 to form a discontinuous emitter band. The diameter of at least the emitter band 918 may be tailored to fit into catheters of various sizes, for example, by compressing the semi-annular shaped emitter band 918.

In some examples, the shock wave emitter assembly 902 may include several emitter bands 918 disposed along a length of the shock wave emitter assembly 902. One or more of the emitter bands 918 may be disposed on a same side of the shock wave emitter assembly 902. Additionally or alternatively, one or more of the emitter bands 918 may be disposed on opposing sides of the shock wave emitter assembly 902, for example, to emit shock waves in different directions. The one or more emitter bands 918 disposed on opposing sides of the shock wave emitter assembly 902 may be disposed in an alternating fashion. One or more of the emitter bands on the same side of the shock wave emitter assembly 902 may be disposed substantially next to each other. Additionally or alternatively, one or more of the emitter bands 918 (on the same and/or opposing sides of the shock wave emitter assembly 902) may be separated, for example, by an attachment portion (e.g., similar to attachment portion 924 described above). Additional configurations of shock wave emitter assemblies that include one or more discontinuous emitter bands are described in greater detail in U.S. Patent Application 63/599,950, the contents of which are incorporated herein in its entirety.

Figure 10A:
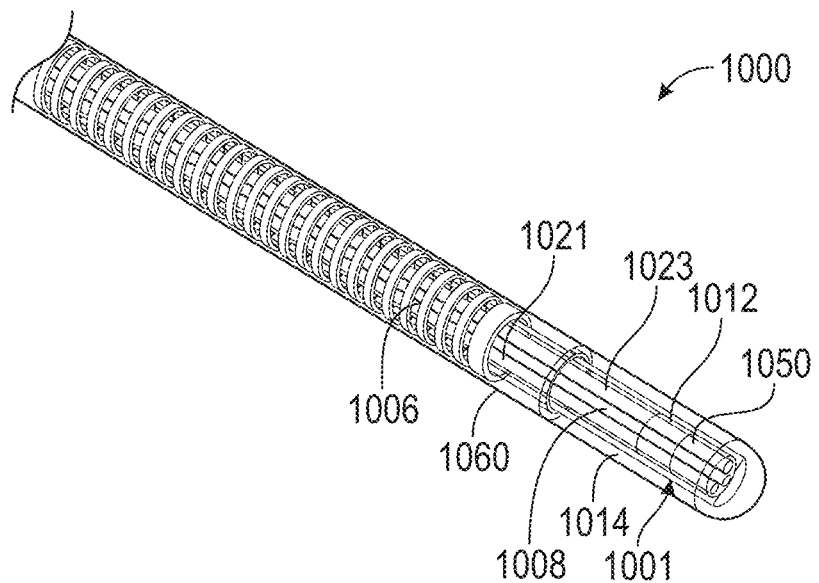
FIG. 10A illustrates a perspective view of a distal portion of an exemplary shock wave catheter that includes a distally emitting shock wave emitter, according to one or more aspects of the present disclosure.
Figure 10B:
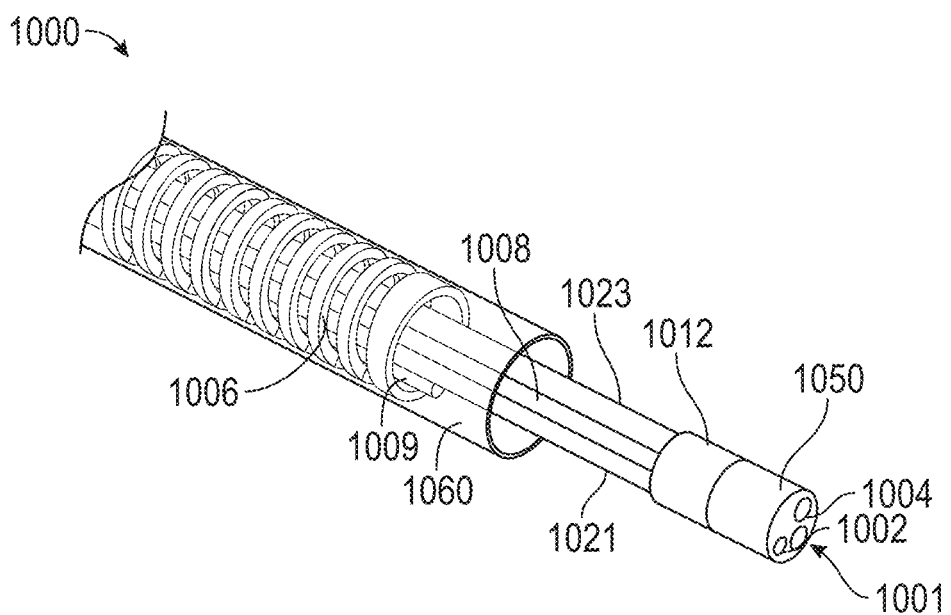
FIG. 10B illustrates another perspective view of the shock wave catheter of FIG. 10A, with the enclosure of the shock wave catheter removed, according to one or more aspects of the present disclosure.
Figure 10C:
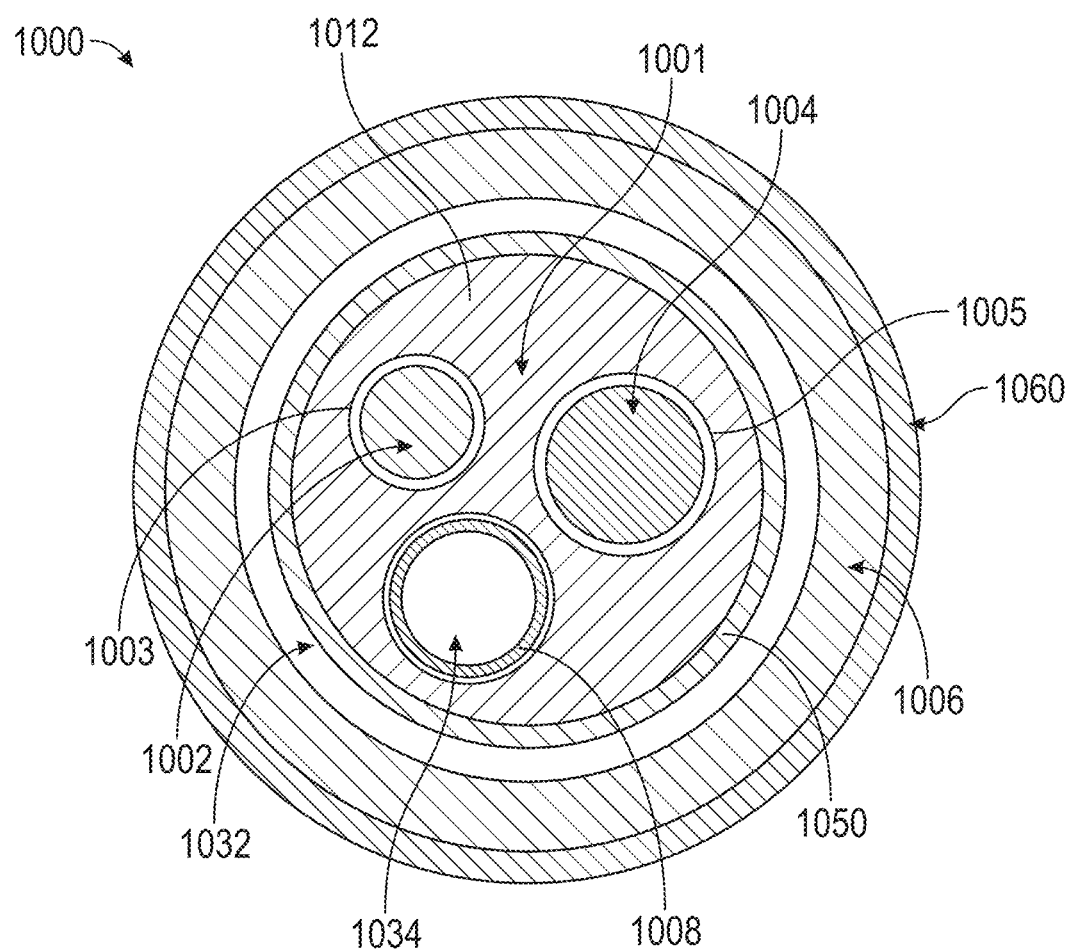
FIG. 10C illustrates a cross-sectional view of the shock wave catheter of FIGS. 10A-10B through a distal tip of the shock wave catheter, according to one or more aspects of the present disclosure.

FIGS. 10A-10C illustrate another exemplary shock wave catheter 1000 that is used without a guidewire and can be used for the shock wave catheter 100 in shock wave system 150. FIG. 10B illustrates the shock wave catheter 1000 that is illustrated in FIG. 10A, however, in FIG. 10B, the enclosure 1014 at the distal end of the shock wave catheter 1000 is removed. FIG. 10C illustrates a cross-sectional view of the shock wave catheter 1000 through a distal tip 1012 of the shock wave catheter 1000 (with the enclosure 1014 removed).

Like the shock wave catheters described above, the catheter 1000 includes at least one shock wave emitter 1001 disposed distal to the elongate tube 1006 in the shock wave catheter 1000. The at least one shock wave emitter 1001 can be distally spaced from the distal end of the elongate tube 1006. The shock wave emitter 1001 can be formed by a pair of electrodes 1002 and 1004. In some examples, the shock wave catheter 1000 includes only a single shock wave emitter 1001 formed by a single pair of electrodes 1002, 1004 to minimize the crossing profile of the shock wave catheter 1000. Each of the electrodes 1002, 1004 can be electrically connected to a pulse generator, such as by conductive wires 1021 and 1023 extending within the shock wave catheter 1000 from a proximal portion of the shock wave catheter 1000 to a distal portion of the shock wave catheter 1000. For example, the conductive wires 1021 and 1023 can extend through the elongate tube 1006 of the shock wave catheter 1000 from the distal tip 1012 to a control hub connected to the proximal portion of the shock wave catheter 1000. In some examples, one or more of the conductive wires 1021 and 1023 can extend through the elongate tube 1006 to the at least one shock wave emitter 1001.

In some examples, the electrodes 1002 and 1004 can be provided by the distal ends of the conductive wires 1021 and 1023. One of the distal ends of the conductive wires (e.g., conductive wire 1021) can form a positive electrode (e.g., electrode 1002) and the other of the distal end (e.g., of conductive wire 1023) can form a negative electrode (e.g., electrode 1004). In some embodiments, these polarities may be switched during use of the shock wave catheter 1000 so that the electrodes 1002 and 1004 wear out evenly. In some embodiments, a conductive wire having a negative polarity (e.g., conductive member 1023) can be thicker than a conductive wire having a positive polarity (e.g., conductive member 1021) such that the electrode with negative polarity has a larger surface area than the electrode with positive polarity. In some embodiments, one electrode (e.g., electrode 1004) has a surface area that is at least 25% larger than the other electrode (e.g., electrode 1002). In some embodiments, one electrode (e.g., electrode 1004) has a surface area that is up to 150% larger than the other electrode (e.g., electrode 1002). The conductive wire having the negative polarity may be thicker than the conductive wire having the positive polarity so that when higher energy is applied to the electrodes 1002 and 1004 connected thereto (or formed by the distal ends thereof), the emitter gap between the electrodes 1002 and 1004 remains constant for a longer amount of time. In contrast, if the conductive wires are the same size, the emitter gap may change unfavorably, in turn shortening the life of the shock wave catheter 1000 by quickly diminishing the possible sonic output therefrom. In some embodiments, the electrode 1004 (e.g., the negative electrode) has a greater surface area than the electrode 1002 (e.g., the positive electrode). When a voltage pulse is applied across the spark gap defined by the space between the electrodes 1002 and 1004 (e.g., the distal ends of the conductive wires 1021 and 1023), the shock wave emitter 1001 generates a shock wave that propagates away from the shock wave emitter 1001 (e.g., in a distal direction).

In some examples, the shock wave catheter 1000 may include one or more energy guides (e.g., similar to conductive wire 1021 and/or 1023) that are an optical fiber configured to electrically couple to a laser source (e.g., a pulse generator configured to generate laser pulses). In this manner, the shock wave catheter 1000 may be configured to generate shock waves based on one or more laser pulses generated by the pulse generator coupled to the at least one energy guide.

The conductive wires 1021 and 1023 can be made of a metal or a metal alloy. In some embodiments, one or more of the conductive wires 1021 and 1023 are made, at least in part, of a refractory metal, such as molybdenum, niobium, or tantalum. In some embodiments, one or more of the conductive wires 1021 and 1023 are made, at least in part, of a nickel-chromium superalloy. In some embodiments, one or more of the conductive wires 1021 and 1023 are made of an electrically conductive material that has a melting point above 2000 degrees Centigrade (Celsius). In some embodiments, one of the conductive wires 1021 and 1023 (e.g., a conductive wire having a negative polarity, such as the conductive wire 1023) is made at least in part of a refractory metal and the other conductive wire (e.g., a conductive wire having a positive polarity, such as the conductive wire 1021) is made of a non-refractory metal or alloy (e.g., copper, gold, or steel). In some embodiments, one or more of the conductive wires 1021 and 1023 are formed in part of a non-refractory metal and in part (e.g., at their distal ends to form the electrodes 1002 and 1004) of a refractory metal. Including refractory metals as electrodes for shock wave catheters can beneficially increase device life, because refractory metals degrade much slower than non-refractory metals (e.g., steel or copper). However, such an implementation of refractory metals may not be feasible in thicker, conventional shock wave catheters, because these metals generally have higher resistivity and hardness (and, thus, malleability) than typical wire materials such as copper. On the other hand, advantageously, employing refractory metal wires along an entire length of the shock wave catheter (e.g., from a proximal region of the catheter to the electrode or electrodes) avoids the need for additional manufacturing steps for electrically connecting the wires to other non-refractory metal wires (e.g., to form an electrode).

As illustrated in FIG. 10C, shock wave catheter 1000 includes a pair of fluid lumens 1032 and 1034 that extend through the elongate tube 1006. The fluid lumen 1032 may be formed at least in part by the outer member 1060 surrounding the elongate tube 1008 and the enclosure 1014 surrounding at least the shock wave emitter 1001. The fluid lumen 1034 may be formed by a tubular member 1008 extending within the elongate tube 1006 from a control hub at the proximal portion of the shock wave catheter 1000 to the distal tip 1012 of the shock wave catheter 1000. Fluid lumen 1032 may extend to the enclosure 1014 to introduce fluid (e.g., saline, contrast, or a mixture thereof) into the chamber enclosed by enclosure 1014. Fluid lumen 1034 may also extend to the enclosure 1014, but may be used to purge fluid or bubbles that form through electrolysis during shock wave generation. In some embodiments, these functions of the fluid lumens 1032 and 1034 may be reversed. The fluid lumen 1032 may surround at least the fluid lumen 1034.

In some embodiments, as shown in FIG. 10B, the shock wave catheter 1000 can include a core wire 1009 extending within the elongate tube 1006 and terminating at the distal end of the elongate tube 1006. I core wire 1009 can extend from the control hub coupled to the proximal portion of the shock wave catheter 1000, the control hub including a switch coupled to the core wire 1009 for bending and deflecting at least the distal tip 1012 of the shock wave catheter 1000.

The distal tip 1012 can include fluid lumen 1032 and additional lumens 1003, 1005 for receiving a portion of conductive wires 1021 and 1023 (i.e., at least the electrodes 1002, 1004). In this manner, the distal tip 1012 can at least partially surround the shock wave emitter 1001 formed by the ends of the conductive wires 1021 and 1023. The distal tip 1012 can aid in maintaining the proper distance between the ends of the conductive wires 1021, 1023 (and therefore the spark gap distance.) In some examples, distal tip 1012 helps to maintain the position and orientation of shock wave emitter 1001 during use so that shock waves generated during therapy have consistent power and direction of propagation. As shown in FIGS. 10A-10B, the distal tip 1012 may be spaced from the distal end of elongate tube 1006. In some examples, the distal tip 1012 may be made of a polymeric material. For example, the distal tip 1012 may be composed of a material having a Shore hardness less (softer) than 100 D. A radiopaque marker 1050 can be mounted on a surface of the distal tip 1012 for visualizing the location of the shock wave emitter 1001 during use of the shock wave catheter 1000 (e.g., via fluoroscopy). For example, the radiopaque marker 1050 may be in the form of a band or ring that wraps around at least a portion of the distal tip 1012. In some embodiments, the radiopaque marker 1050 is longitudinally aligned with the electrodes 1002 and 1004 in the shock wave catheter 1000 to indicate the location of the electrodes 1002 and 1004 of the shock wave emitter 1001 during use of the shock wave catheter 1000. In some examples, the radiopaque marker 1050 is disposed proximal to the distal end of the shock wave emitter 1001 to prevent interference of the radiopaque marker 1050 with the propagation of shock waves from the shock wave emitter 1001.

Shock wave catheter 1000 may include an outer member 1060 that at least partially surrounding the elongate tube 1006 and forms an outer layer of the shock wave catheter 1000. The enclosure 1060 may be made of a polymeric material. The outer member 1060 (surrounding the elongate tube 1006) and the enclosure 1014 (enclosing at least the shock wave emitter 1001) may be formed integrally, or may be formed as discrete members that are adhered to each other. The enclosure 1014 may define an internal volume (that is fillable with fluid) less than 1.5 cubic centimeters ($cm^3$). In some embodiments, the internal volume of the enclosure 1014 is between 0.25 $cm^3$-1.0 $cm^3$.

At least a portion of the elongate tube 1006 may be a coil that enables the shock wave catheter 1000 to bend and turn through tortuous vessels, similar to the elongate tubes having coiled portions described above. The elongate tube 1006 may be a helical coil that can vary in pitch along its length. For example, the coil may have greater pitch at its distal portion to provide greater flexibility to the distal portion of the elongate tube 1006. In some examples, the coiled portion of the elongate tube 1006 may be formed from a stainless steel hypotube.

Figure 11:
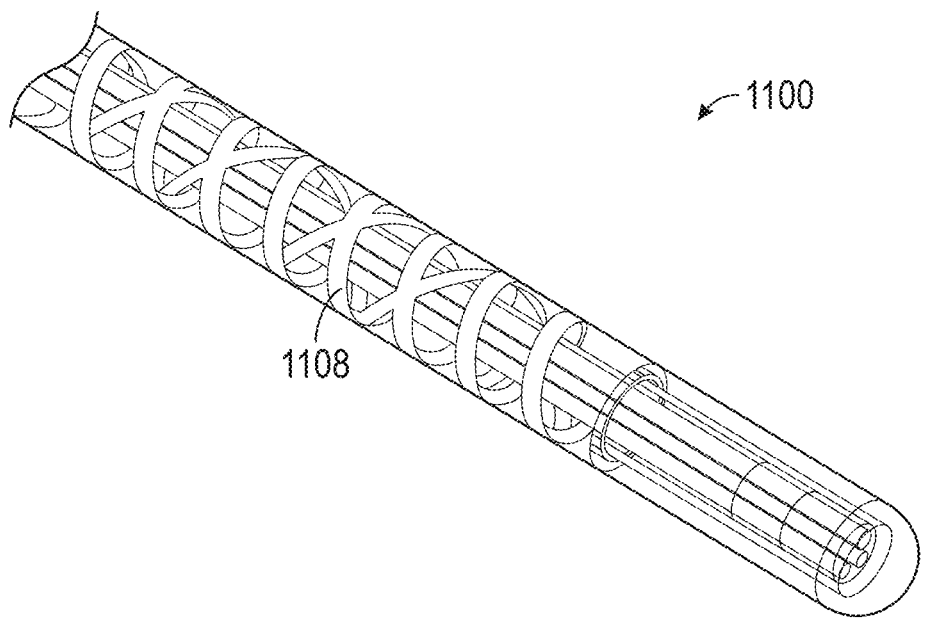
FIG. 11 illustrates an exemplary shock wave catheter having a braided elongate tube, according to one or more aspects of the present disclosure.

In some examples, in addition to or instead of including a coil, at least a portion of the elongate tube of the shock wave catheters described herein can include a braided portion. FIG. 11 illustrates a shock wave catheter 1100 similar to shock wave catheter 1000, but rather than the elongate tube 1108 having a coiled portion, it includes a braided portion. The shock wave catheter 1100 can be used for shock wave catheter 1000 in shock wave system 150. The braided portion of the elongate tube 1108 may be formed from a stainless steel hypotube. The braided portion may provide more stiffness to the elongate tube 1108 than, for example, a coil. Thus, the shock wave catheter 1100 may be preferable over the catheter 1000 when the body lumen to be navigated is less tortuous, and/or when the target lesion is farther from the point of entry and thus requires longer navigation to reach the target lesion.

Figure 12:
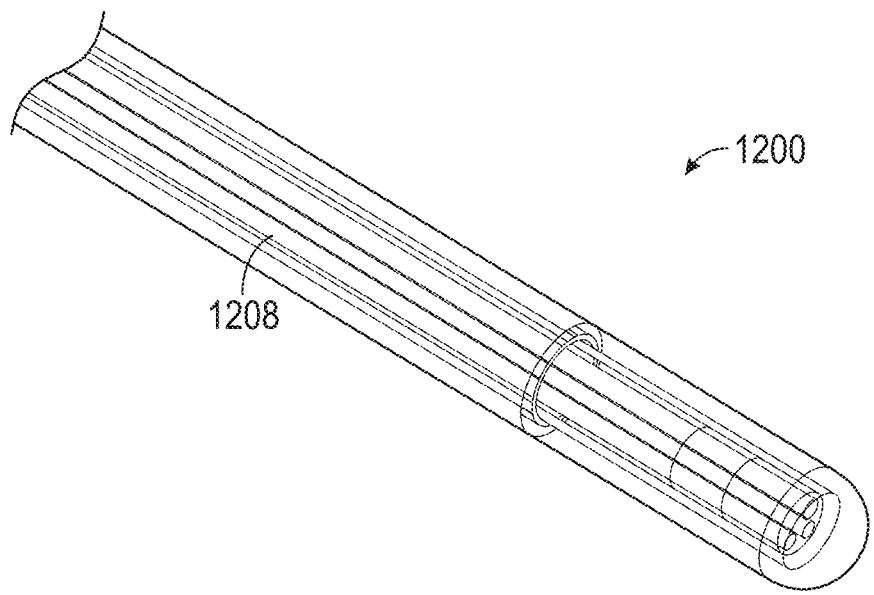
FIG. 12 illustrates an exemplary shock wave catheter having an non-helical elongate tube at least partially surrounded by an outer member, according to one or more aspects of the present disclosure.

FIG. 12 illustrates a shock wave catheter 1200 that is similar to shock wave catheters 1000 and 1100, but includes an elongate tube 1208 that is rigid or partially rigid. The shock wave catheter 1200 can be used for shock wave catheter 100 in shock wave system 150. The elongate tube 1208 may have a continuous surface (i.e., without any cutouts or slits, such as described with respect to the coiled and braided portions in elongate tubes 1006 and 1108). The elongate tube 1208 may be stiffer than an elongate tube having a braided portion and/or a coiled portion, described above, and thus may be used at least for relatively less tortuous vasculature.

Figure 13:
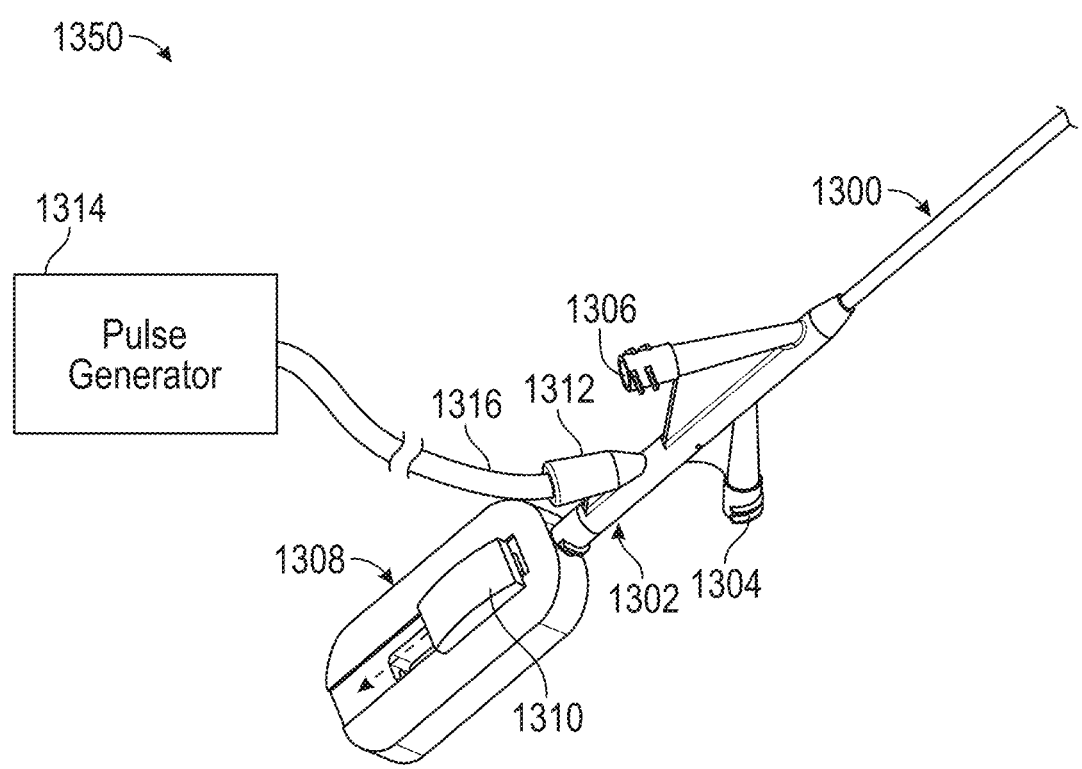
FIG. 13 illustrates a perspective view of an exemplary control hub that is attached to a catheter and receives a switch for controlling the catheter, according to one or more aspects of the present disclosure.

As noted above, the shock wave catheters described herein can be used alongside a control hub that facilitates fluid into and out of the shock wave catheter, as well as connectivity between a pulse generator and the shock wave emitter(s) within the distal portion of the shock wave catheters. FIG. 13 illustrates a proximal region of an exemplary shock wave system 1350 that includes a control hub 1302 attached to the proximal end of a shock wave catheter 1300. The shock wave system 1350 can be used for shock wave system 150 described herein with respect to FIG. 1. The control hub 1302 may not include a port to receive a guidewire because the shock wave catheters used with the control hub 1302 and described throughout may not include a lumen to receive a guidewire.

The control hub 1302 includes a fluid inlet port 1304 and a fluid outlet port 1306 that aspirate and purge the shock wave catheter 1300, respectively. The fluid inlet port 1304 can couple to a fluid source, and the fluid outlet port 1306 can couple to a fluid reservoir. The fluid source may contain a conductive fluid (e.g., saline, deionized water, etc.), an x-ray contrast, or a mixture thereof. The fluid inlet port 1304 and/or fluid outlet port 1306 may connect to tubing and/or one or more connectors (e.g., Luer connectors). In some examples, the fluid inlet port 1304 can connect to a syringe that aspirates the lumen of the shock wave catheter 1300.

The shock wave system 1350 can include a controller 1308 that is coupled to a wire extending within the shock wave catheter 1300 to control deflection and bending of at least the distal tip of the shock wave catheter 1300. For example, with reference to shock wave catheter 700 described above with respect to FIGS. 7A-7E, the controller 1308 can be coupled to the core wire 720. The controller 1308 may be disposed at a proximal end of the control hub 1302, such that the wire of the shock wave catheter 1300 extends through the control hub 1302 and exits the proximal end of the control hub 1302 where it connects to the controller 1308. The controller 1308 includes a switch 1310 that a user may engage, or slide, between several positions on the controller 1308 to cause the distal tip of the catheter to bend and deflect. The switch 1310 may be a slider, knob, thumbwheel, etc. The switch 1310 may be moved along a straight line, as illustrated by the dashed line in FIG. 13. Alternatively, the switch 1310 may be moved along a circle, arc, or other shape on the controller 1308 to control the deflection of the distal tip of the shock wave catheter 700. The switch 1310 can be disposed in a slot in the controller 1308, the length of the slot limiting the movement of the switch 1310. In turn, the degree to which the switch 1310 is moved within the slot can be directly related to the amount of deflection (or bending) of the distal tip of the shock wave catheter 1300. In some examples, when the switch 1310 is in a final position within the slot of the controller 1308, the distal tip of the catheter may be maximally bent in a U-shape or annular shape.

The control hub 1302 includes a port 1312 that facilitates connection between the shock wave emitter(s) within the shock wave catheter 1300 and an external pulse generator 1314. One or more conductive wires may extend within the shock wave catheter 1300 and may be fed through the port 1312 to connect to the external pulse generator 1314. The shock wave system 1350 can include one or more cables 1316 that insulate the conductive wires between the port 1312 and the pulse generator 1314 to prevent damage to the conductive wires.

The pulse generator 1314 can generate energy pulses to cause the shock wave emitter(s) of the shock wave catheter 1300 to generate shock waves. For example, the pulse generator 1314 may generate energy pulses that cause the shock wave emitter(s) to generate shock waves in accordance with a set frequency. An example frequency may be between 1-5 Hz. In some examples, the pulse generator 1314 may be a high voltage source that generates one or more voltage pulses having an amplitude between about 0.5 kV and 10 kV. The pulse width of the applied voltage pulses ranges between two microseconds and six microseconds (2-6 s). The repetition rate or frequency of the applied voltage pulses may be between about 1 Hz and 10 Hz. The total number of pulses applied by the power source 1314 may be, for example, sixty (60) pulses, eighty (80) pulses, one hundred twenty (120) pulses, three hundred (300) pulses, or up to five hundred (500) pulses, or other increments of pulses within this range. In some examples, the pulse generator 1314 may generate one or more bursts of micro-pulses in rapid succession (e.g., with a frequency between about 100 Hz-10 kHz). A series of the bursts of micro-pulses can be generated in accordance with the aforementioned frequency of about 1-5 Hz. Alternatively, the pulse generator 1314 may be a laser, and the conductive wires extending between the shock wave emitter(s) of the shock wave catheter 1300 and the pulse generator 1314 may be optical fibers that couple the laser to the shock wave emitter(s). In this example, the pulse generator 1314 may generate one or more laser pulses that cause the shock wave emitter(s) to generate shock waves. The preferred voltage, repetition rate, and number of pulses may vary depending on, e.g., the size of the lesion, the extent of calcification, the size of the blood vessel, the attributes of the patient, or the stage of treatment. For instance, a physician may start with low energy shock waves and increase the energy as needed during the procedure, or vice versa. The magnitude of the shock waves can be controlled by controlling the voltage, current, duration, and repetition rate of the pulsed voltage from the power source 1314. The amplitude of the energy (e.g., voltage or laser) and frequency of the pulses may vary depending on, e.g., the size of the lesion, the extent of calcification, the size of the blood vessel, attributes of the patient, the emitters being operated, and/or the stage of treatment. For example, a physician may start with low energy shock waves and may increase the energy as needed during the procedure, or vice versa.

Figure 14:
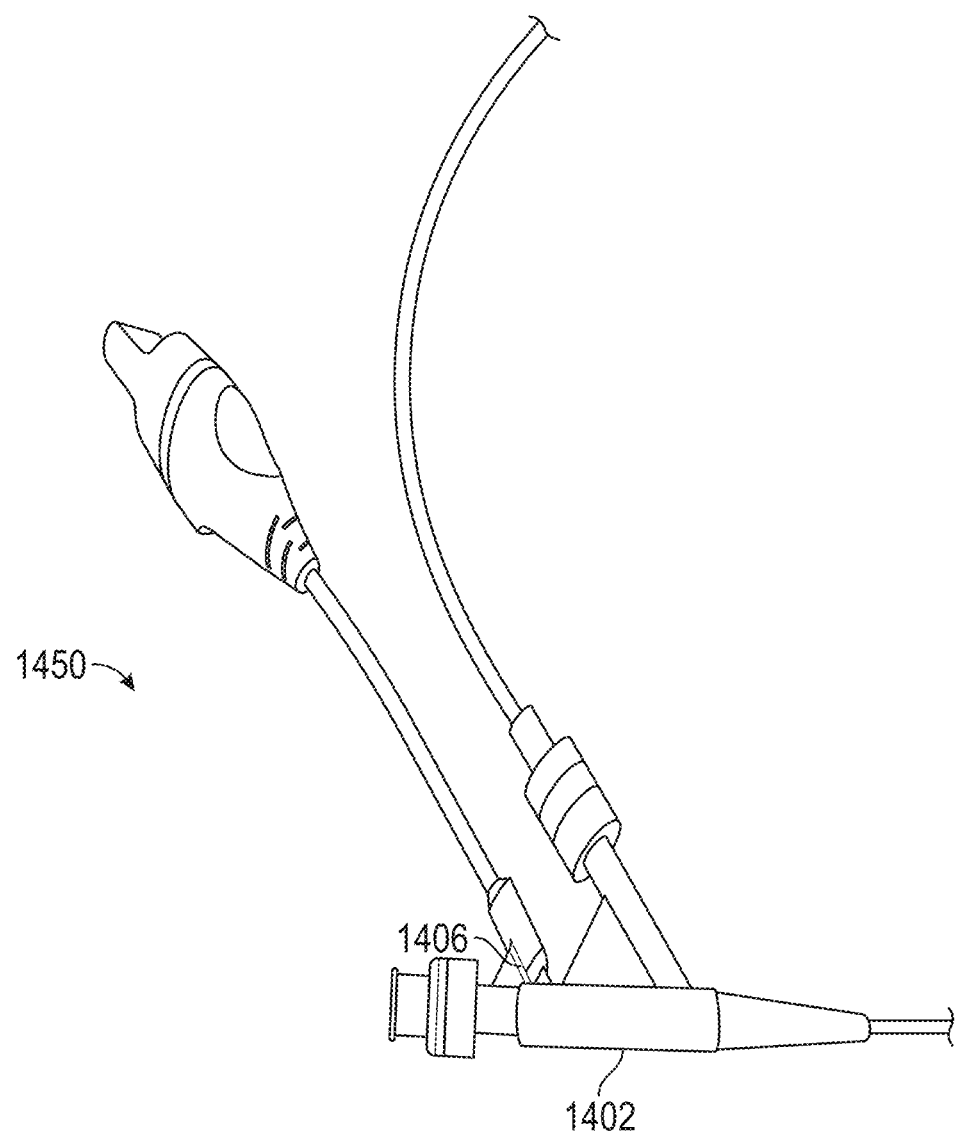
FIG. 14 illustrates a perspective view of an exemplary control hub that is attached to a catheter and includes a fluid outlet having a check valve for controlling fluid removal from the catheter, according to one or more aspects of the present disclosure.

FIG. 14 depicts a proximal region of another exemplary shock wave system 1450 that includes a control hub 1402 attached to the proximal end of a shock wave catheter 1400. The shock wave system 1450 can be used for shock wave system 150 described herein with respect to FIG. 1. Shock wave system 1450 may differ from shock wave system 1350 in that the system may include a fluid outlet port 1406 that includes a check valve for automatically purging/evacuating bubbles that are created due to lithotripsy from the distal end of the catheter and through the shock wave catheter 1400 when a threshold volumetric pressure within the shock wave catheter 1400 is met. Although not explicitly illustrated by FIG. 14, it is to be understood that the shock wave system 1450 can include a controller (e.g., similar to controller 1308) for controlling deflection of the distal tip of the shock wave catheter 1400. The control hub 1402 can facilitate the connection between shock wave emitter(s) within the shock wave catheter 1400 and an external pulse generator (not illustrated).

Figure 15A:
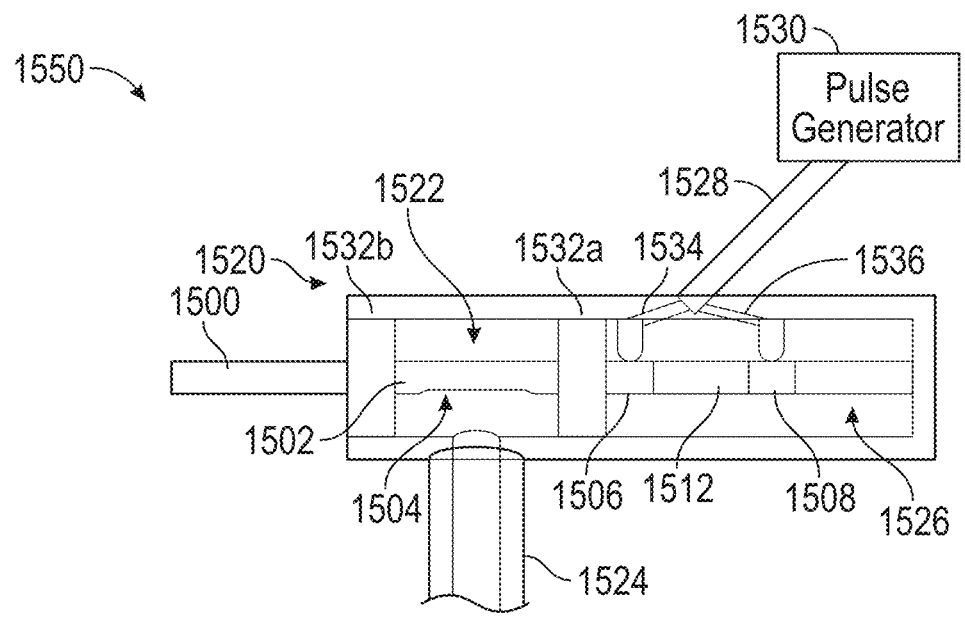
FIG. 15A illustrates a side view of an exemplary control hub that is attached to a catheter and receives a stopcock for controlling fluid flow into and out of the catheter, according to one or more aspects of the present disclosure.
Figure 15B:
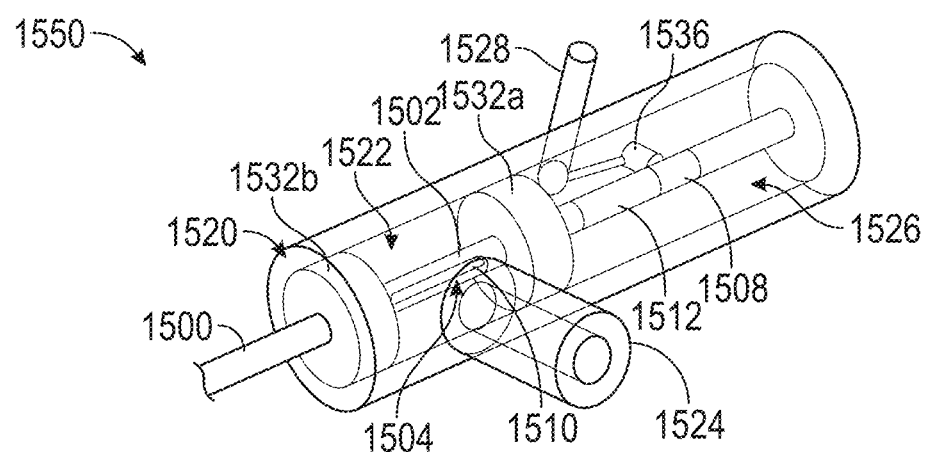
FIG. 15B illustrates a perspective view of the control hub that is attached to a catheter and receives a stopcock for controlling fluid flow into and out of the catheter, according to one or more aspects of the present disclosure.
Figure 16:
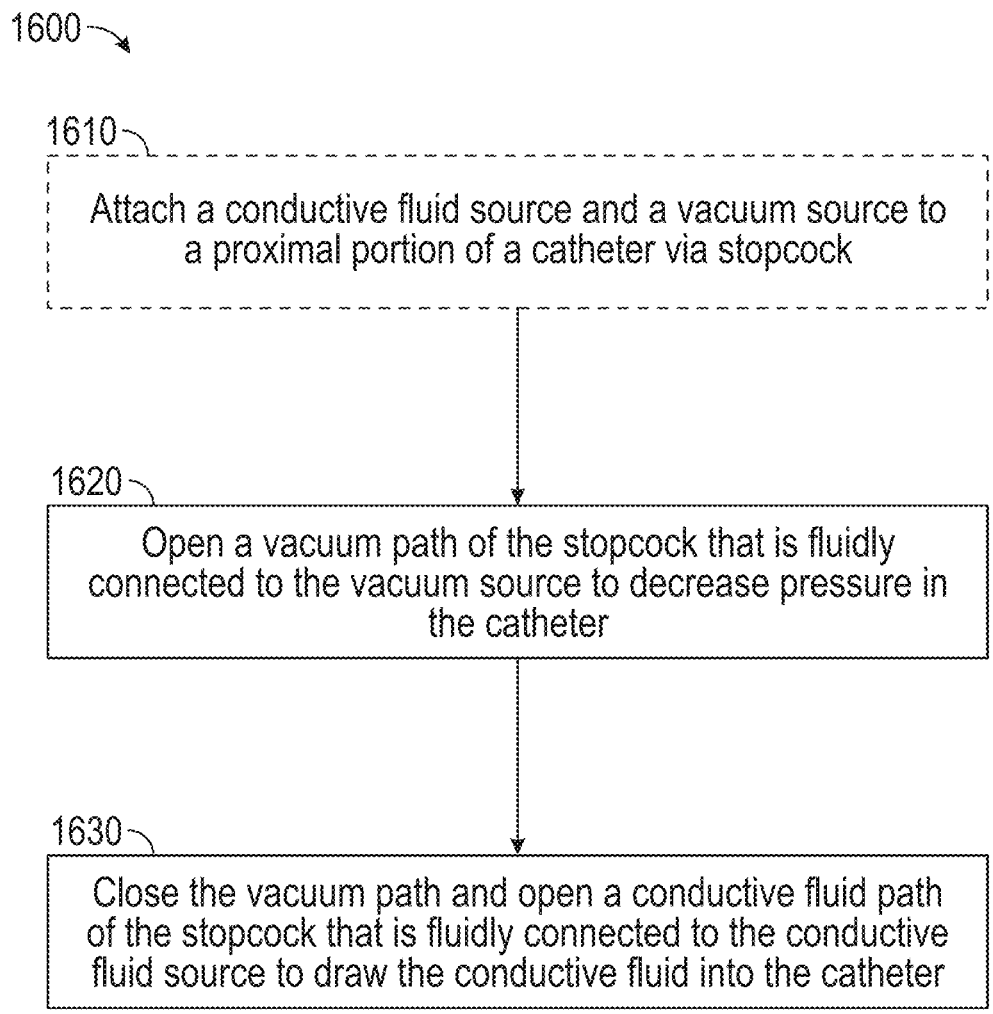
FIG. 16 illustrates an exemplary method for controlling fluid flow into and out of a catheter using a stopcock fluidly connected to the catheter, according to one or more aspects of the present disclosure.

FIGS. 15A-15B illustrate a proximal region of another exemplary shock wave system 1550 that includes a control hub 1520 for aspiration and purging of a shock wave catheter 1500 and connectivity between the shock wave emitter(s) of the shock wave catheter 1500 and a pulse generator 1530. The shock wave system 1550 can be used for shock wave system 150 described with respect to FIG. 1. The control hub 1520 can removably attach to the proximal end of the shock wave catheter 1500. The control hub 1520 can be a hemostasis valve (e.g., a tuohy borst valve), in that it includes a chamber that is divided into different portions that receive specific parts of the shock wave catheter 1500 and facilitates secure connection between these specific parts of the catheter and different devices. For example, the control hub 1520 includes a fluid-receiving portion 1522 that fluidly connects a lumen of the shock wave catheter 1500 to a fluid source (e.g., via a fluid port 1224 extending therefrom). The elongate tube 1502 of the shock wave catheter 1500 can include at least one opening 1504 that provides access to the lumen of the elongate tube 1502 of the shock wave catheter 1500. The portion of the shock wave catheter 1500 that includes the opening 1504 is disposed within the fluid-receiving portion 1522 of the control hub 1520 to enable aspiration and purging of the lumen of the shock wave catheter 1500.

The control hub 1520 also includes an electrical connection portion 1526 that electrically connects the conductive portions 1506, 1508 of the shock wave catheter 1500 to a pulse generator 1530 (e.g., via a port 1528 extending therefrom). The electrical connection portion 1526 of the control hub 1520 can include a set of electrical contacts 1534, 1536 that electrically connect to each of the conductive portions 1506, 1508, respectively. One electrical contact (e.g., electrical contact 1534) may transmit voltage from the shock wave catheter 1500, whereas the other (e.g., electrical contact 1536) may transmit voltage from the pulse generator 1530 to the shock wave catheter 1500. The conductive portions 1506, 1508 of the shock wave catheter 1500 can be the elongate tube 1502 and the core wire 1510 themselves, for example, in the instance the elongate tube 1502 and the core wire 1510 are conductive (e.g., as described above with respect to shock wave catheter 500 in FIG. 5). Alternatively, one or more of the conductive portions 1506, 1508 can be a contact pad that enables electrical connection between the conductive elongate tube 1502, core wire 1510 and the electrical contacts 1534, 1536 (respectively). In the shock wave system 1550, the elongate tube 1502 forms the conductive portion 1506, and the conductive portion 1508 is a contact pad that facilitates connection between the electrical contact 1536 and narrow core wire 1510. The conductive portions 1506, 1508 of the shock wave catheter 1500 may be separated from one another by an insulator 1512 that prevents shorting of the electrical circuit between the conductive portions 1506, 1508 (and the electrical contacts 1534, 1536). Without limitation, the insulator can be polyimide, thermoplastic polyurethane, PTFE, another insulating polymer, or a ceramic.

The fluid-receiving portion 1522 and the electrical connection portion 1526 of the control hub 1520 may be divided from one another by a pressure seal 1532a. The electrical connection portion 1526 (and the port 1528 extending therefrom) can be disposed proximal to the pressure seal 1532a, whereas the fluid-receiving portion 1522 (and the fluid port 1524 extending therefrom) can be disposed distal to the pressure seal 1532a. The pressure seal 1532a can receive the shock wave catheter 1500 but can also prevent any fluid within the fluid-receiving portion 1522 from entering the electrical connection portion 1526 and damaging the electrical connections. The control hub 1520 can include another pressure seal 1532b at the distal end of the fluid-receiving portion 1522 that is substantially identical to the pressure seal 1532a in that it receives the shock wave catheter 1500 and prevents any fluid from leaving the fluid-receiving portion 1522 of the control hub 1520. The pressure seals 1532a, 1532b can be a polymer (e.g., PTFE) or a rubber-like material (e.g., silicone).

Although the control hub 1520 is described above with respect to FIGS. 15A-15B as including both a fluid-receiving portion 1522 and an electrical connection portion 1526, it is to be understood that an exemplary control hub 1520 may include just one of these portions. For example, an exemplary control hub 1520 may include a fluid-receiving portion 1522 in conjunction with a port 1528 that facilitates connectivity between the external pulse generator 1530 and conductive wires extending within the shock wave catheter 1500. The port 1528 and fluid-receiving portion 1522 may be sealed from one another, for example, by a pressure seal 1532a. In this manner, the control hub 1520 may be usable with other types of guidewireless shock wave catheters and is not limited to shock wave catheters including a conductive elongate tube and core wire (e.g., shock wave catheter 500 described above with respect to FIG. 5). For example, the control hub 1520 may be usable with a laser energy-based shock wave system in which the pulse generator 1530 is a laser, and the shock wave catheter 1550 includes optical fibers extending therewithin.

Figure 17A:
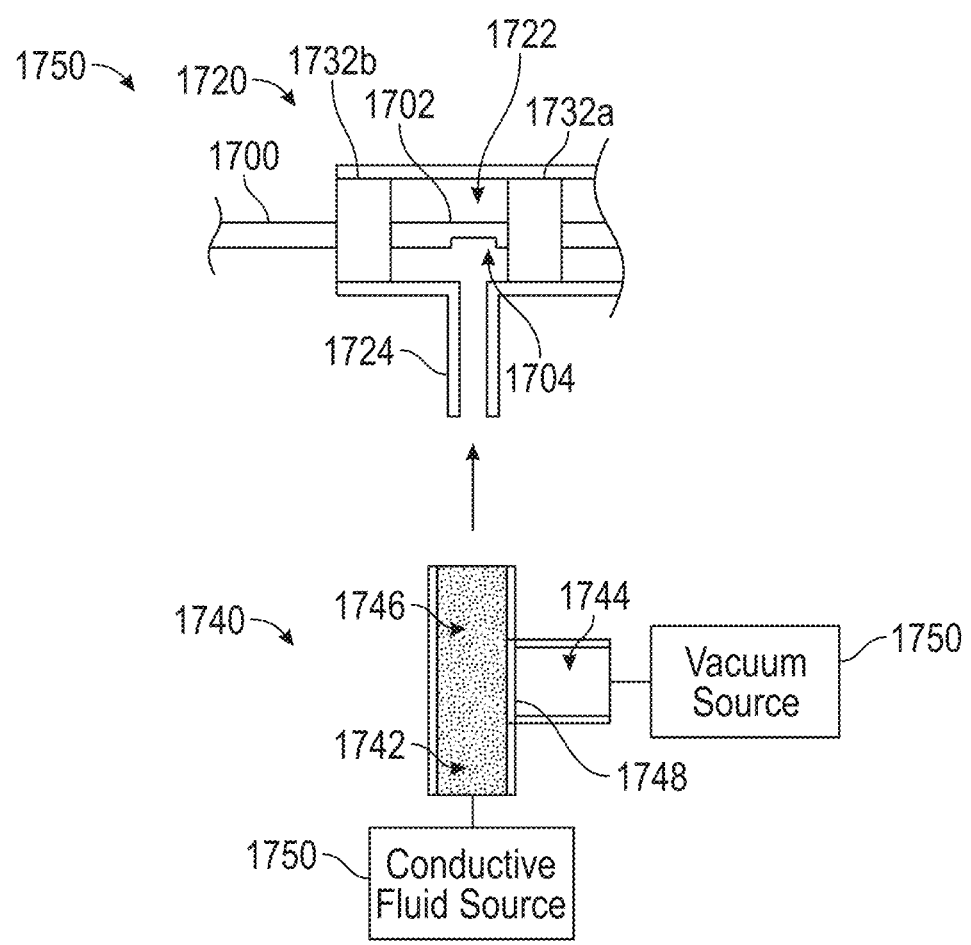
FIG. 17A illustrates attaching a stopcock to a control hub that is attached to a catheter, according to one or more aspects of the present disclosure.
Figure 17B:
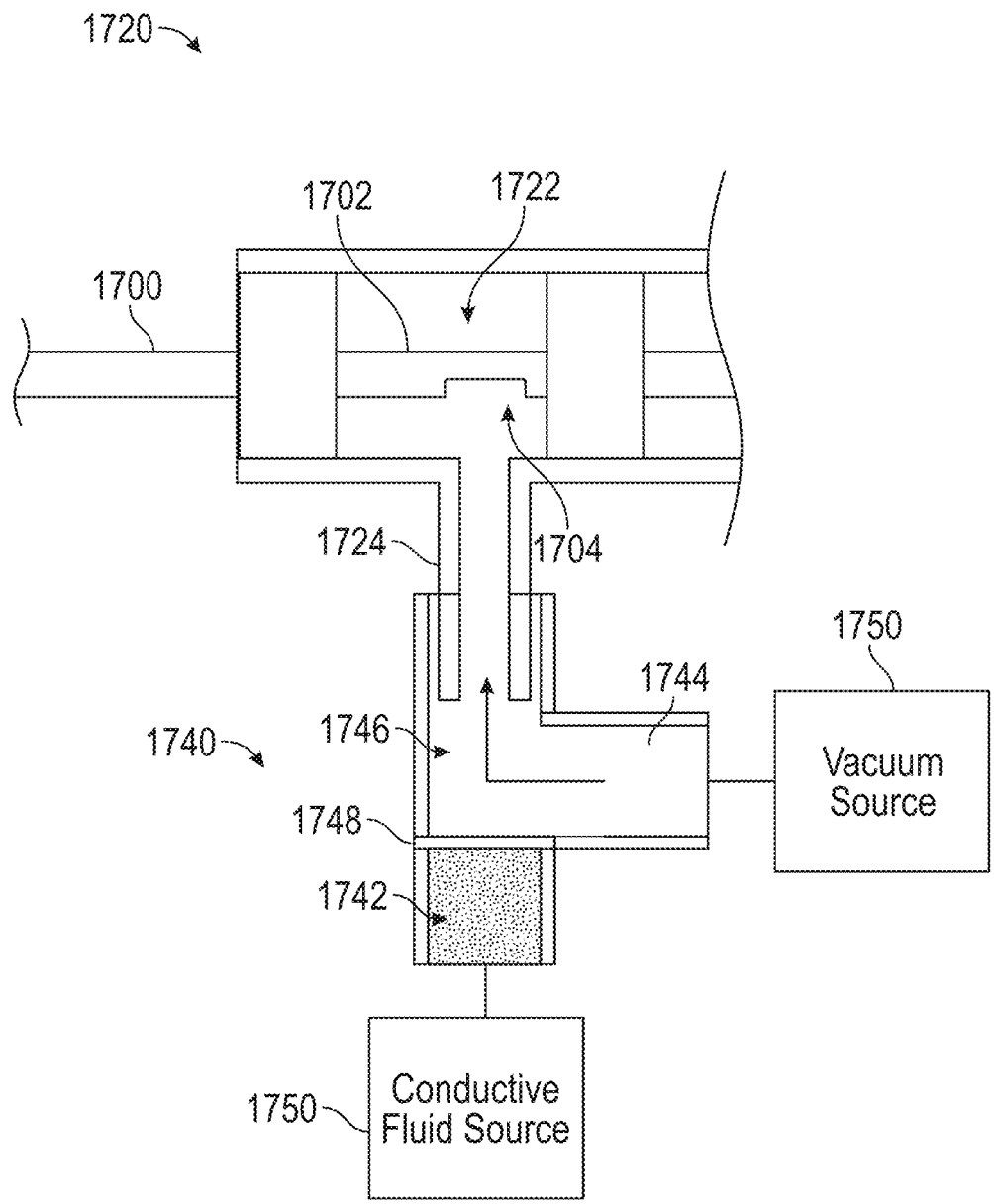
FIG. 17B illustrates introducing vacuum pressure to the control hub and attached catheter via the stopcock, according to one or more aspects of the present disclosure.
Figure 17C:
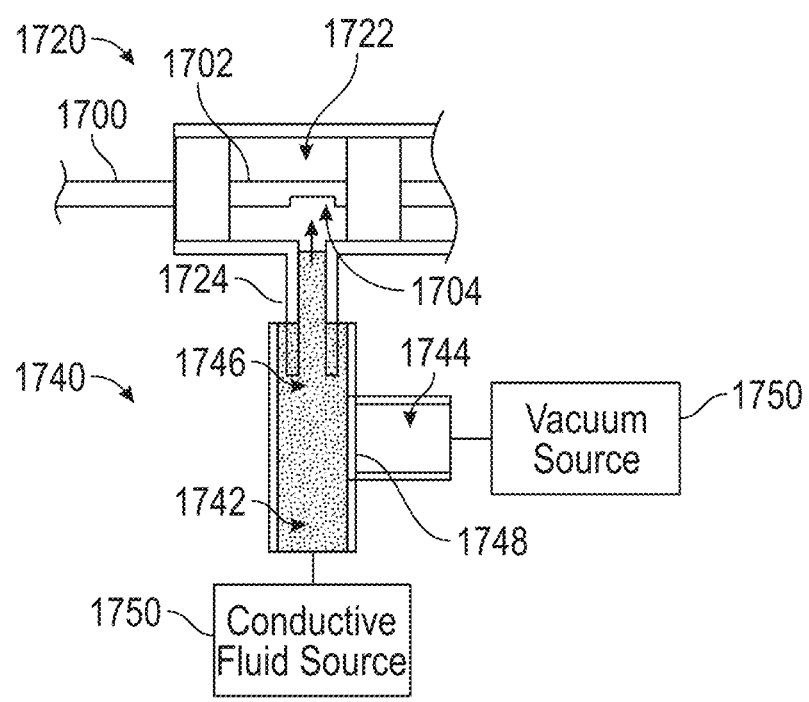
FIG. 17C illustrates introducing fluid to the control hub and attached catheter via the stopcock, according to one or more aspects of the present disclosure.

As noted above, the fluid port 1524 of the control hub 1520 may connect directly to a fluid source or may connect to a fluid source via tubing and/or connectors. Alternatively, the fluid port 1524 may connect to a fluid source using a stopcock that can control fluid flow to and from the shock wave catheter 1500. FIG. 16 depicts a method 1600 for aspirating and purging a shock wave catheter, such as the shock wave catheter 1500 in shock wave system 1550. FIGS. 17A-17C depict a control hub 1720 and stopcock 1740 and are used to illustrate the various steps of the method 1600. The control hub 1720 can be used for at least a portion of the control hub 1520 in shock wave system 1550.

At block 1610, the method 1600 can include attaching a conductive fluid source and a vacuum source to a proximal portion of a catheter via a stopcock. FIG. 17A illustrates an example of attaching a stopcock 1740 to a shock wave catheter 1700, the stopcock connected to a vacuum source 1750 and conductive fluid source 1760. The stopcock 1740 includes a conductive fluid path 1742, a vacuum path 1744, and a central path 1746 that interchangeably connects to the conductive fluid path 1742 and the vacuum path 1744 by engaging a valve 1748 of the stopcock 1740. At least the central path 1746 of the stopcock 1740 may be primed, for example, with a saline solution (represented by the dotted pattern in the central path 1746 of the stopcock 1740 in FIG. 17A). A control hub 1720 removably attached to the proximal portion of the shock wave catheter 1700 includes a fluid-receiving portion 1722 in which an opening 1704 in the elongate tube 1702 of the shock wave catheter 1700 is disposed within. A fluid port 1724 extending from the fluid-receiving portion 1722 of the control hub 1720 can removably receive (or can be inserted into) the primed stopcock 1740. The connection between the stopcock 1740 and the fluid port 1724 can be secured by pressure seals 1732*a*, 1732*b* within the chamber of the control hub 1720.

At block 1620, the method 1600 includes opening the vacuum path of the stopcock that is fluidly connected to the vacuum source to decrease the pressure in the shock wave catheter. FIG. 17B illustrates an example of opening the vacuum path 1744 of the stopcock 1740 to decrease the pressure in the shock wave catheter 1700. The valve 1748 of the stopcock 1740 can be actuated to block off the conductive fluid path 1742 and cause the vacuum pressure (represented by the arrow extending from the vacuum path 1744 into the central path 1746) from the connected vacuum source 1750 to enter into the elongate tube 1702 of the shock wave catheter 1700 via the opening 1704 in the tube. Blocking off the conductive fluid path 1742 can cause any conductive fluid held within the conductive fluid path 1742 to pressurize to a high level of pressure suitable to drive the conductive fluid path 1742 into the shock wave catheter 1700 when the conductive fluid path 1742 and shock wave catheter 1700 are fluidly connected.

At block 1630, the method 1600 includes closing the vacuum path and subsequently opening the conductive fluid path of the stopcock that is fluidly connected to the conductive fluid source to draw conductive fluid into the shock wave catheter. FIG. 17C illustrates an example of closing the vacuum path 1744 and opening the conductive fluid path 1742 of the stopcock 1740 to draw the conductive fluid into the shock wave catheter 1700. The valve 1748 can be actuated to block off the vacuum path 1744, in turn opening the conductive fluid path 1742 to the central path 1746 of the stopcock 1740. The negative pressure in the elongate tube 1702 of the shock wave catheter 1700 and the fluid-receiving portion 1722 of the control hub 1720 can cause the highly pressurized conductive fluid from the conductive fluid source (represented by the dotted pattern within the fluid port 1724 and the stopcock 1740) to be automatically drawn into the fluid-receiving portion 1722 and through the elongate tube 1702 of the shock wave catheter 1700 via the opening 1704. The conductive fluid travels through the lumen of elongate tube 1702 to the distal portion of the elongate tube where shock wave emitter(s) are disposed for shock wave generation. The shock wave catheter 1700 may draw the conductive fluid into the elongate tube 1702 until the pressure between the shock wave catheter 1700, the fluid-receiving portion 1722 of the control hub 1720, and the stopcock 1740 (i.e., the system) settles to a constant pressure that is suitable for shock wave delivery by the shock wave catheter 1700. For example, the pressure may be between about 1-6 atm.

Figure 18:
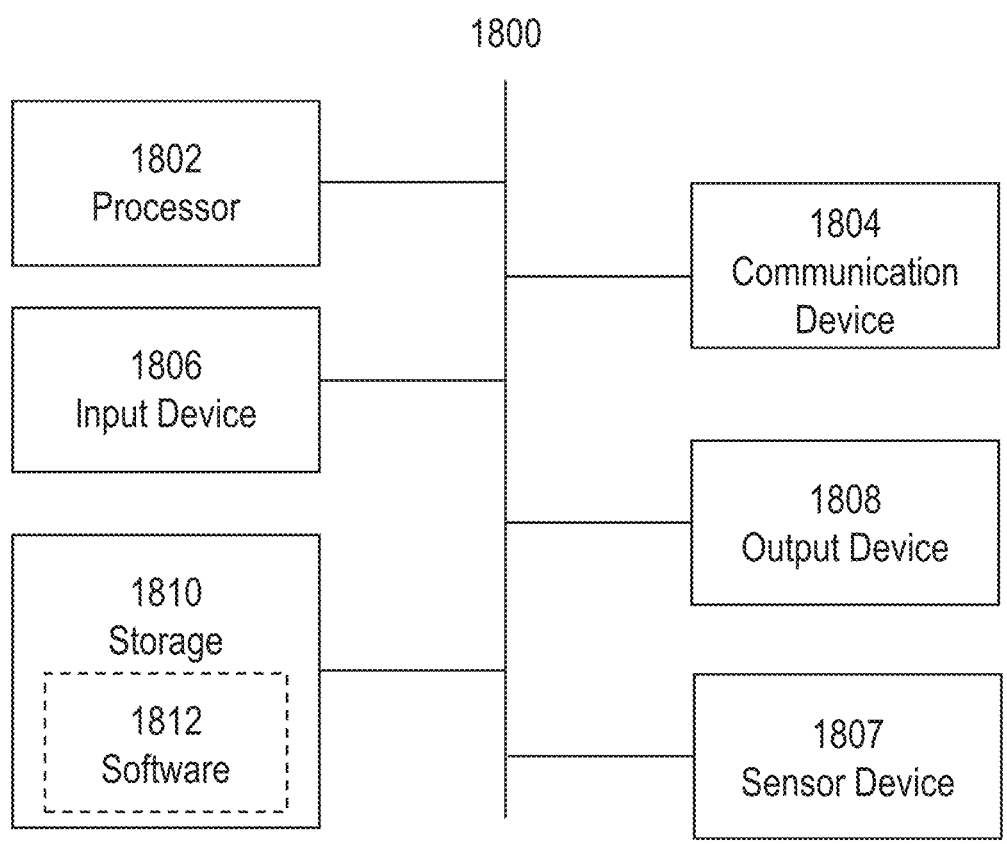
FIG. 18 illustrates an exemplary computing system, according to one or more aspects of the present disclosure.

FIG. 18 depicts an exemplary computing device 1800 which may form part of the system 100 described above and may be used for performing various steps of the methods described herein, in accordance with one or more examples of the disclosure. Device 1800 can be a host computer connected to a network. Device 1800 can be a client computer or a server. As shown in FIG. 18, device 1800 can be any suitable type of microprocessor-based device, such as a personal computer, workstation, server, or handheld computing device (i.e., a portable electronic device) such as a phone or tablet. The device can include, for example, one or more of processors 1802, input device 1806, sensor device 1807, output device 1808, storage 1810, and communication device 1804. Input device 1806 and output device 1808 can generally correspond to those described above and can either be connectable or integrated with the computer.

Input device 1806 can be any suitable device that provides directed input, such as a touch screen, keyboard or keypad, mouse, or voice-recognition device, in other words, input or directions provided or initiated by a user. Sensor device 1807 can be one or more of any suitable sensor devices, such as a pressure sensor, a thermal sensor, an electrical sensor (e.g., current, voltage, resistance, and/or impedance sensors), or a visualization element. Output device 1808 can be any suitable device that provides output, such as a touch screen, haptics device, or speaker. Storage 1810 can be any suitable device that provides storage, such as an electrical, magnetic, or optical memory, including a RAM, cache, hard drive, or removable storage disk. Communication device 1804 can include any suitable device capable of transmitting and receiving signals over a network, such as a network interface chip or device. The components of the computer can be connected in any suitable manner, such as via a physical bus or wirelessly.

Sensor devices 1807 can provide feedback to an operator using device 1800 by measuring parameters in the surrounding environment and thereby indicating a status of the device 1800, and further providing for guidance on what further steps the operator may decide to implement with device 1800. For example, in implementations where sensor devices 1807 include pressure sensors, a slight decrease in pressure may indicate success at cracking a calcified lesion, due to the fact that the expandable member surrounding the emitters is able to further expand without changing the volume of fluid within the expandable member. Further, a significant decrease in pressure may indicate a rupture failure mode where the expandable member has lost seal and fluid volume, and thus guiding toward withdrawal of the device. In implementations where the sensor devices include a visualization element, an operator of the device 700 may be able to more clearly understand where the device 1800 is located relative to a target lesion or anatomy, prior to, during, and after delivering therapy.

Software 1812, which can be stored in storage 1810 and executed by processor 1802, can include, for example, the programming that embodies the functionality of the present disclosure (e.g., as embodied in the devices as described above). Software 1812 can also be stored and/or transported within any non-transitory computer-readable storage medium for use by, or in connection with, an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1810, that can contain or store programming for use by, or in connection with, an instruction execution system, apparatus, or device. Software 1812 can also be propagated within any transport medium for use by, or in connection with, an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by, or in connection with, an instruction execution system, apparatus, or device. The transport-readable medium can include, but is not limited to, an electronic, magnetic, optical, electromagnetic, or infrared wired or wireless propagation medium.

Device 1800 may be connected to a network, which can be any suitable type of interconnected communication system. The network can implement any suitable communication protocols and can be secured by any suitable security protocols. The network can comprise network links of any suitable arrangement that can implement the transmission and reception of network signals, such as wireless network connections, T1 or T3 lines, cable networks, DSL, or telephone lines. Device 1800 can implement any operating system suitable for operating on the network. Software 1812 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

EXEMPLARY EMBODIMENTS

The following embodiments are exemplary and are not intended to limit the scope of any invention described herein.

Embodiment 1. A shock wave catheter for treating a lesion of a body lumen, the shock wave catheter comprising:
   an elongate tube;
   a core wire extending within the elongate tube and fixed to a distal end of the elongate tube;
   at least one shock wave emitter disposed distal to the elongate tube and configured to generate at least one shock wave; and
   an enclosure surrounding at least a portion of the elongate tube and enclosing the at least one shock wave emitter.

Embodiment 2. The shock wave catheter of embodiment 1, wherein the elongate tube comprises at least one window so that the at least one shock wave can propagate through the at least one window.

Embodiment 3. The shock wave catheter of embodiment 2, wherein the at least one window is disposed on a side of the elongate tube, such that the at least one shock wave generated by the at least one shock wave emitter is emitted from the side of the elongate tube.

Embodiment 4. The shock wave catheter of any one of embodiments 1-3, wherein the at least one shock wave emitter is disposed at the distal end of the elongate tube, such that the at least one shock wave generated by the at least one shock wave emitter is emitted from the distal end of the elongate tube.

Embodiment 5. The shock wave catheter of any one of embodiments 1-4, wherein the core wire comprises an elongate portion that extends within the elongate tube and a distal tip fixed to the distal end of the elongate tube, the distal tip comprising a larger diameter than the elongate portion of the core wire.

Embodiment 6. The shock wave catheter of any one of embodiments 1-5, wherein at least a portion of the elongate tube comprises a coil or a plurality of slits.

Embodiment 7. The shock wave catheter of any one of embodiments 1-6, wherein the enclosure is fillable with a conductive fluid.

Embodiment 8. The shock wave catheter of any one of embodiments 1-7, wherein the enclosure encloses the distal end of the elongate tube.

Embodiment 9. The shock wave catheter of any one of embodiments 1-8, wherein the enclosure extends a length of the elongate tube to surround the elongate tube.

Embodiment 10. The shock wave catheter of any one of embodiments 1-8, wherein at least a portion of the elongate tube proximal to the enclosure is coated.

Embodiment 11. The shock wave catheter of any one of embodiments 1-10, wherein the shock wave catheter does not comprise a guidewire lumen.

Embodiment 12. The shock wave catheter of any one of embodiments 1-11, comprising at least one conductive wire configured to electrically couple the at least one shock wave emitter to a pulse generator.

Embodiment 13. The shock wave catheter of embodiment 12, wherein the at least one shock wave emitter comprises an electrode pair, and a distal end of the at least one conductive wire forms an electrode of the electrode pair.

Embodiment 14. The shock wave catheter of embodiment 12, wherein the at least one conductive wire comprises an optical fiber configured to electrically couple to a laser.

Embodiment 15. A system for treating a lesion of a body lumen, comprising:
   the shock wave catheter of any one of embodiments 1-14; and
   a pulse generator coupled to the at least one shock wave emitter and configured to generate energy pulses to cause the at least one shock wave emitter to generate the at least one shock wave.

Embodiment 16. The system of embodiment 15, wherein the pulse generator is configured to generate the energy pulses to cause the at least one shock wave emitter to generate a series of shock waves in accordance with a frequency between 1 Hz and 5 Hz.

Embodiment 17. The system of embodiment 15 or 16, wherein the pulse generator is configured to generate one or more voltage pulses to cause the at least one shock wave emitter to generate the at least one shock wave.

Embodiment 18. The system of embodiment 17, wherein the one or more voltage pulses comprises a voltage between 0.5 kV and 10.0 kV.

Embodiment 19. The system of embodiment 15 or 16, wherein the pulse generator is configured to generate one or more laser pulses to cause the at least one shock wave emitter to generate the at least one shock wave.

Embodiment 20. A shock wave catheter for treating a lesion of a body lumen, the shock wave catheter comprising:
   an elongate tube;
   a wire extending within the elongate tube and terminating proximate to a distal end of the elongate tube;
   a shock wave emitter formed by the distal end of the elongate tube and at least a portion of the wire and configured to generate at least one shock wave; and an enclosure enclosing the shock wave emitter.

Embodiment 21. The shock wave catheter of embodiment 20, wherein at least a distal portion of the elongate tube comprises a plurality of slits or a coil.

Embodiment 22. The shock wave catheter of embodiment 20 or 21, wherein the enclosure is fillable with a conductive fluid.

Embodiment 23. The shock wave catheter of any one of embodiments 20-22, wherein the enclosure comprises at least one window so that the at least one shock wave can propagate through the at least one window.

Embodiment 24. The shock wave catheter of any one of embodiments 20-23, wherein the enclosure surrounds at least a portion of the elongate tube.

Embodiment 25. The shock wave catheter of any one of embodiments 20-23, wherein the elongate tube is coated with an electrically insulating coating.

Embodiment 26. The shock wave catheter of any one of embodiments 20-25, wherein the elongate tube comprises nitinol.

Embodiment 27. The shock wave catheter of any one of embodiments 20-26, wherein the conductive wire comprises at least one of molybdenum, copper, or a mixture thereof.

Embodiment 28. The shock wave catheter of any one of embodiments 20-27, wherein the elongate tube has an outer diameter between 0.25-0.5 mm.

Embodiment 29. The shock wave catheter of any one of embodiments 20-28, wherein the elongate tube has an inner diameter between 0.1-0.4 mm.

Embodiment 30. The shock wave catheter of any one of embodiments 20-29, wherein the wire comprises an optical fiber configured to electrically couple to a laser.

Embodiment 31. The shock wave catheter of any one of embodiments 20-30, wherein the shock wave catheter does not comprise a guidewire lumen.

Embodiment 32. A system for treating a lesion of a body lumen, comprising:
  the shock wave catheter of any one of embodiments 20-31; and
  a pulse generator coupled to the shock wave emitter and configured to generate energy pulses to cause the shock wave emitter to generate the at least one shock wave.

Embodiment 33. The system of embodiment 32, wherein the pulse generator is configured to generate the energy pulses in accordance with a frequency between 1 Hz and 5 Hz.

Embodiment 34. The system of embodiment 32 or 33, wherein the pulse generator is configured to generate one or more voltage pulses to cause generation of the at least one shock wave.

Embodiment 35. The system of embodiment 34, wherein the one or more voltage pulses comprises a voltage between 0.5 kV and 10.0 kV.

Embodiment 36. The system of embodiment 32 or 33, wherein the pulse generator is configured to generate one or more laser pulses to cause generation of the at least one shock wave.

Embodiment 37. The system of any one of embodiments 32-36, wherein a proximal portion of the elongate tube comprises at least one opening to a lumen of the elongate tube, the lumen fluidly connected to the enclosure, and wherein the system comprises:
  a control hub connected to the proximal portion of the elongate tube, the control hub comprising:
    at least one pressure seal enclosing the at least one opening of the elongate tube; and
    a fluid port fluidly connected to the at least one opening of the elongate tube, to a vacuum pressure source, and to a conductive fluid source to (a) decrease pressure within at least one of the lumen of the elongate tube and the enclosure, and (b) subsequently draw conductive fluid into at least one of the lumen of the elongate tube and the enclosure.

Embodiment 38. The system of embodiment 37, wherein the control hub comprises a port configured to connect the pulse generator to the wire and the elongate tube.

Embodiment 39. The system of embodiment 38, wherein the port is disposed proximal to the at least one pressure seal of the control hub to electrically connect to the elongate tube and to the wire at a location proximal to the at least one opening of the elongate tube.

Embodiment 40. The system of any one of embodiments 37-39, wherein the fluid port fluidly connects to the vacuum pressure source and the conductive fluid source via a stopcock.

Embodiment 41. A shock wave catheter for treating a lesion of a body lumen, the shock wave catheter comprising:
  a shock wave emitter assembly comprising:
    a first shock wave emitter configured to emit at least one distally directed shock wave; and
    a second shock wave emitter disposed proximal to the first shock wave emitter, the second shock wave emitter configured to emit at least one laterally directed shock wave;
  an elongate tube coupled to the shock wave emitter assembly; and
  an enclosure enclosing the coupled shock wave emitter assembly and elongate tube.

Embodiment 42. The shock wave catheter of embodiment 41, wherein the elongate tube comprises a variable pitch flat wire coil, a pitch of a proximal portion of the coil being greater than a pitch of a distal portion of the coil.

Embodiment 43. The shock wave catheter of embodiment 41 or 42, wherein the elongate tube has an outer diameter no greater than 1 mm.

Embodiment 44. The shock wave catheter of any one of embodiments 41-43, wherein at least one of the first shock wave emitter and the second shock wave emitter comprise an annular emitter band.

Embodiment 45. The shock wave catheter of any one of embodiments 41-44, wherein the elongate tube comprises one or more of stainless steel, nitinol, tool steel, and titanium.

Embodiment 46. The shock wave catheter of any one of embodiments 41-45, wherein the enclosure comprises one or more of Pebax®, nylon, Tecothane™, Texin®, and polyurethane.

Embodiment 47. The shock wave catheter of any one of embodiments 41-46, wherein the outer diameter of the elongate tube is between 0.75-1 mm.

Embodiment 48. The shock wave catheter of any one of embodiments 41-47, wherein a distal end of the enclosure is closed.

Embodiment 49. The shock wave catheter of any one of embodiments 41-48, wherein the shock wave catheter does not comprise a guidewire lumen.

Embodiment 50. The shock wave catheter of any one of embodiments 41-49, comprising at least one conductive wire configured to electrically couple the first shock wave emitter and the second shock wave emitter to a pulse generator.

Embodiment 51. The shock wave catheter of embodiment 50, wherein:
  the first shock wave emitter comprises a first electrode pair;
  the second shock wave emitter comprises a second electrode pair; and the at least one conductive wire comprises:
    a first conductive wire comprising a distal end forming an electrode of the first electrode pair; and
    a second conductive wire comprising a distal end forming an electrode of the second electrode pair.

Embodiment 52. The shock wave catheter of embodiment 51, wherein the first conductive wire and the second conductive wire are each individually connected to a pulse generator.

Embodiment 53. The shock wave catheter of embodiment 51, wherein the first conductive wire and the second conductive wire are connected to each other.

Embodiment 54. The shock wave catheter of embodiment 51, wherein the at least one conductive wire comprises at least one optical fiber configured to electrically couple to a laser.

Embodiment 55. A system for treating a lesion of a body lumen, comprising:
- the shock wave catheter of any one of embodiments 41-54; and
- a pulse generator coupled to the first shock wave emitter and to the second shock wave emitter and configured to generate energy pulses to cause the first shock wave emitter and the second shock wave emitter to generate the shock waves.

Embodiment 56. The system of embodiment 55, wherein the pulse generator is configured to generate the energy pulses to cause at least one of the first shock wave emitter and the second shock wave emitter to generate a series of shock waves in accordance with a frequency between 1 Hz and 5 Hz.

Embodiment 57. The system of embodiment 55 or 56, wherein the pulse generator is configured to generate one or more voltage pulses to cause at least one of the first shock wave emitter and the second shock wave emitter to generate the shock wave.

Embodiment 58. The system of embodiment 57, wherein the one or more voltage pulses comprises a voltage between 0.5 kV and 10.0 kV.

Embodiment 59. The system of embodiment 55 or 56, wherein the pulse generator is configured to generate one or more laser pulses to cause at least one of the first shock wave emitter and the second shock wave emitter to generate the shock wave.

Embodiment 60. The system of any one of embodiments 55-59, comprising a switch coupled to a distal portion of the shock wave catheter via a core wire extending through the shock wave catheter and connected to the distal portion of the shock wave catheter to control deflection of the distal portion of the shock wave catheter.

Embodiment 61. The system of embodiment 60, comprising a control hub connected to a proximal portion of the shock wave catheter and configured to receive the core wire coupling the switch and the distal portion of the shock wave catheter.

Embodiment 62. The system of embodiment 61, wherein the control hub comprises:
- at least one fluid port connected to a lumen of the shock wave catheter to aspirate and purge the lumen; and
- a port that facilitates connection of the pulse generator to the first shock wave emitter and the second shock wave emitter.

Embodiment 63. A method for treating a lesion of a body lumen, comprising:
- advancing a shock wave catheter through the body lumen without use of a guidewire such that at least one shock wave emitter enclosed within an enclosure of the shock wave catheter is disposed proximate to the lesion of the body lumen; and
- generating at least one shock wave by the at least one shock wave emitter to treat the lesion.

Embodiment 64. The method of embodiment 63, wherein the shock wave catheter is the shock wave catheter of any one of embodiments 1-62.

Embodiment 65. The method of embodiment 63, wherein the shock wave catheter comprises a core wire extending within the shock wave catheter and coupled to a distal portion of the shock wave catheter and to a switch at a proximal end of the shock wave catheter, and the method comprises engaging the switch to control deflection of the distal portion of the shock wave catheter.

Embodiment 66. The method of any one of embodiments 63-65, comprising, prior to generating the at least one shock wave, filling the enclosure with a conductive fluid.

Embodiment 67. The method of any one of embodiments 63-66, wherein generating the at least one shock wave by the at least one shock wave emitter comprises generating one or more energy pulses by a pulse generator electrically coupled to the at least one shock wave emitter, the one or more energy pulses causing the at least one shock wave emitter to generate the at least one shock wave.

Embodiment 68. The method of embodiment 67, wherein generating the one or more energy pulses by the pulse generator comprises generating a series of energy pulses that cause the at least one shock wave emitter to generate a series of shock waves in accordance with a frequency between 1 Hz and 5 Hz.

Embodiment 69. The method of embodiment 67 or 68, wherein generating the one or more energy pulses by the pulse generator comprises generating one or more voltage pulses that cause the at least one shock wave emitter to generate the at least one shock wave.

Embodiment 70. The method of embodiment 69, wherein the one or more voltage pulses comprises a voltage between 0.5 kV and 10.0 kV.

Embodiment 71. The method of embodiment 67 or 68, wherein generating the one or more energy pulses by the pulse generator comprises generating one or more laser pulses that cause the at least one shock wave emitter to generate the at least one shock wave.

Embodiment 72. The method of any one of embodiments 63-71, wherein the lesion comprises a stent embedded within the lumen.

Embodiment 73. The method of any one of embodiments 63-72, comprising using the shock wave catheter as a guidewire for a balloon catheter device.

Embodiment 74. A method for modulating pressure in a shock wave shock wave catheter, comprising:
- opening a vacuum path of a stopcock that is fluidly connected to a vacuum source and to a lumen of the shock wave shock wave catheter to decrease pressure in the shock wave shock wave catheter;
- closing the vacuum path of the stopcock; and
- opening a conductive fluid path of the stopcock that is fluidly connected to a conductive fluid source and to the lumen of the shock wave shock wave catheter to draw conductive fluid from the conductive fluid source into the lumen of the shock wave shock wave catheter.

Embodiment 75. The method of embodiment 74, wherein the stopcock is fluidly connected to the lumen of the shock wave catheter via a control hub comprising:
- at least one pressure seal enclosing at least one opening of the shock wave shock wave catheter that is fluidly connected to the lumen; and
- a fluid port fluidly connected to the at least one opening and attached to the stopcock to fluidly connect the vacuum source and the conductive fluid source to the lumen of the shock wave shock wave catheter.

Embodiment 76. The method of embodiment 75, wherein the control hub comprises a port that connects one or more conductive portions of the shock wave shock wave catheter to a pulse generator.

Embodiment 77. The method of embodiment 76, wherein the port is disposed proximal to the at least one pressure seal of the control hub to electrically connect to the one or more conductive portions of the shock wave shock wave catheter at a location proximal to the at least one opening of the shock wave shock wave catheter.

Embodiment 78. A shock wave catheter for treating a lesion of a body lumen, the shock wave catheter comprising:
- an elongate tube;
- at least one shock wave emitter disposed distal to the elongate tube and configured to generate at least one shock wave;
- a distal tip disposed at or proximate to a distal end of the at least one shock wave emitter; and
- an enclosure enclosing at least the at least one shock wave emitter.

Embodiment 79. The shock wave catheter of embodiment 78, wherein at least a portion of the elongate tube comprises a coil or a plurality of slits.

Embodiment 80. The shock wave catheter of embodiment 78 or 79, wherein at least a portion of the elongate tube comprises a braided portion.

Embodiment 81. The shock wave catheter of any one of embodiments 78-80, comprising a core wire extending within the elongate tube and terminating proximate to a distal end of the elongate tube, wherein the core wire is configured to control deflection of at least a distal portion of the shock wave catheter.

Embodiment 82. The shock wave catheter of embodiment 81, wherein a distal end of the core wire comprises the distal tip, and the distal tip has a larger diameter than an elongate portion of the core wire extending within the elongate tube.

Embodiment 83. The shock wave catheter of any one of embodiments 78-82, wherein an internal volume of the enclosure is less than 1.5 cm$^3$.

Embodiment 84. The shock wave catheter of any one of embodiments 78-83, comprising at least one conductive wire configured to electrically couple the at least one shock wave emitter to a pulse generator.

Embodiment 85. The shock wave catheter of embodiment 84, wherein the at least one shock wave emitter comprises an electrode pair and the at least one conductive wire comprises a pair of conductive wires, wherein a distal end of each conductive wire of the pair of conductive wires forms an electrode of the electrode pair.

Embodiment 86. The shock wave catheter of embodiment 84 or 85, wherein the at least one conductive wire extends through the elongate tube to the at least one shock wave emitter and comprises a refractory metal.

Embodiment 87. The shock wave catheter of any one of embodiments 78-83, comprising an optical fiber optically coupled to the at least one shock wave emitter.

Embodiment 88. The shock wave catheter of any one of embodiments 78-87, comprising a radiopaque marker disposed proximate to the at least one shock wave emitter for viewing the at least one shock wave emitter.

Embodiment 89. The shock wave catheter of any one of embodiments 78-88, comprising a first fluid lumen configured to fill the enclosure, and a second fluid lumen configured to remove gas bubbles from the enclosure that are generated during shock wave generation.

Embodiment 90. The shock wave catheter of any one of embodiments 78-88, wherein the at least one shock wave emitter is configured to emit at least one distally directed shock wave when an energy pulse is supplied to the at least one shock wave emitter.

Embodiment 91. The shock wave catheter of any one of embodiments 78-90, wherein an outer diameter of the shock wave catheter is between 0.25-1 mm.

Embodiment 92. The shock wave catheter of any one of embodiments 78-91, wherein the shock wave catheter does not include a guidewire lumen.

Embodiment 93. The shock wave catheter of any one of embodiments 78-92, wherein the distal tip is configured to maintain a position and orientation of the at least one shock wave emitter during use.

Embodiment 94. The shock wave catheter of any one of embodiments 78-93, wherein the elongate tube comprises a variable pitch flat wire coil, a pitch of a proximal portion of the coil being greater than a pitch of a distal portion of the coil.

Embodiment 95. A system for treating a lesion of a body lumen, comprising:
- a shock wave catheter comprising:
  - an elongate tube;
  - at least one shock wave emitter disposed distal to the elongate tube and configured to generate at least one shock wave;
  - a distal tip disposed at or proximate to a distal end of the shock wave emitter; and
  - an enclosure enclosing at least the shock wave emitter; and
- a pulse generator coupled to the at least one shock wave emitter and configured to generate energy pulses to cause the at least one shock wave emitter to generate the at least one shock wave.

Embodiment 96. The system of embodiment 95, wherein the pulse generator is configured to generate the energy pulses with a frequency between 1 Hz and 5 Hz.

Embodiment 97. The system of embodiment 95 or 96, wherein the pulse generator is configured to generate one or more voltage pulses with a voltage between 0.5 kV and 10.0 kV.

Embodiment 98. The system of embodiment 95 or 96, wherein the pulse generator is configured to generate one or more laser pulses to cause the at least one shock wave emitter to generate the at least one shock wave.

Embodiment 99. The system of any one of embodiments 95-98, wherein the shock wave catheter comprises a core wire extending within the elongate tube and terminating proximate to a distal end of the elongate tube, and the system comprises a switch coupled to the core wire to control deflection of a distal portion of the shock wave catheter.

Embodiment 100. The system of embodiment 99, comprising a control hub connected to a proximal portion of the elongate tube and configured to receive the core wire, the core hub comprising:
- at least one fluid port connected to a lumen of the elongate tube via at least one opening in the elongate tube to aspirate and purge the lumen; and
- a port that facilitates connection of the pulse generator to the at least one shock wave emitter.

Embodiment 101. The system of embodiment 100, wherein the control hub comprises at least one pressure seal enclosing the at least one opening of the elongate tube, and wherein the fluid port fluidly connects to a vacuum pressure source and to a conductive fluid source to (a) decrease pressure within at least one of the lumen of the elongate tube and the enclosure, and (b) subsequently draw conductive fluid into at least one of the lumen of the elongate tube and the enclosure.

Embodiment 102. A method for crossing a stent embedded in a body lumen, the method comprising:

advancing a shock wave catheter through the body lumen to the stent without use of a guidewire such that at least one shock wave emitter of the shock wave catheter is disposed proximate to the embedded stent; and generating at least one shock wave by the at least one shock wave emitter.

The electrode assemblies and catheter devices described herein may be used for treating coronary occlusions, such as lesions in arteries and other vessels and a variety of occlusions, such as occlusions in the peripheral vasculature (e.g., above-the-knee, below-the-knee, iliac, carotid, etc.). Catheters having small crossing profiles, such as those described above, may be useful for treating smaller vessels or those that are typically difficult to access, such as the M1, M2, or M3 segments of the middle cerebral artery. For further examples, similar designs may be used for treating soft tissues, such as cancer and tumors (i.e., non-thermal ablation methods), blood clots, fibroids, cysts, organs, scar and fibrotic tissue removal, or other tissue destruction and removal. Electrode assembly and catheter designs could also be used for neurostimulation treatments, targeted drug delivery, treatments of tumors in body lumens (e.g., tumors in blood vessels, the esophagus, intestines, stomach, or vagina), wound treatment, non-surgical removal, and destruction of tissue, or used in place of thermal treatments or cauterization for venous insufficiency and fallopian ligation (i.e., for permanent female contraception).

In one or more examples, the electrode assemblies and catheters described herein could also be used for tissue engineering methods, for instance, for mechanical tissue decellularization to create a bioactive scaffold in which new cells (e.g., exogenous or endogenous cells) can replace the old cells; introducing porosity to a site to improve cellular retention, cellular infiltration/migration, and diffusion of nutrients and signaling molecules to promote angiogenesis, cellular proliferation, and tissue regeneration similar to cell replacement therapy. Such tissue engineering methods may be useful for treating ischemic heart disease, fibrotic liver, fibrotic bowel, and traumatic spinal cord injury (SCI). For instance, for the treatment of spinal cord injury, the devices and assemblies described herein could facilitate the removal of scarred spinal cord tissue, which acts like a barrier for neuronal reconnection, before the injection of an anti-inflammatory hydrogel loaded with lentivirus to genetically engineer the spinal cord neurons to regenerate.

The elements and features of the exemplary electrode assemblies and catheters discussed above may be rearranged, recombined, and modified, without departing from the present invention. Furthermore, numerical designators such as "first", "second", "third", "fourth", etc. are merely descriptive and do not indicate a relative order, location, or identity of elements or features described by the designators. For instance, a "first" shock wave may be immediately succeeded by a "third" shock wave, which is then succeeded by a "second" shock wave. As another example, a "third" emitter may be used to generate a "first" shock wave and vice versa. Accordingly, numerical designators of various elements and features are not intended to limit the disclosure and may be modified and interchanged without departing from the subject invention.

It should be noted that the elements and features of the example catheters illustrated throughout this specification and drawings may be rearranged, recombined, and modified without departing from the present invention. For instance, while this specification and drawings describe and illustrate catheters having several example electrode arrangements, the present disclosure is intended to include catheters having a variety of electrode arrangements. The number, placement, and spacing of the electrode pairs of the shock wave emitters can be modified without departing from the subject invention.

It should be understood that the foregoing is only illustrative of the principles of the invention, and that various modifications, alterations and combinations can be made by those skilled in the art without departing from the scope and spirit of the invention. Any of the variations of the various catheters disclosed herein can include features described by any other catheters or combination of catheters herein. Furthermore, any of the methods can be used with any of the catheters disclosed. Accordingly, it is not intended that the invention be limited, except as by the appended claims.

What is claimed is:

1. A shock wave catheter for treating a lesion of a body lumen, the shock wave catheter comprising:
    an elongate tube;
    at least one shock wave emitter disposed distal to the elongate tube and configured to generate at least one shock wave;
    a core wire extending within the elongate tube and terminating proximate to a distal end of the elongate tube, wherein the core wire is configured to control deflection of at least a distal portion of the shock wave catheter, and wherein a distal end of the core wire comprises a distal tip disposed at or proximate to a distal end of the at least one shock wave emitter, the distal tip having a larger diameter than an elongate portion of the core wire extending within the elongate tube; and
    an enclosure enclosing at least the at least one shock wave emitter.

2. The shock wave catheter of claim 1, wherein at least a portion of the elongate tube comprises a coil or a plurality of slits.

3. The shock wave catheter of claim 1, wherein at least a portion of the elongate tube comprises a braided portion.

4. The shock wave catheter of claim 1, wherein an internal volume of the enclosure is less than 1.5 cm$^3$.

5. The shock wave catheter of claim 1, wherein the shock wave catheter does not include a guidewire lumen.

6. The shock wave catheter of claim 1, comprising a pair of conductive wires, wherein the at least one shock wave emitter comprises an electrode pair and a distal end of each conductive wire of the pair of conductive wires forms an electrode of the electrode pair.

7. The shock wave catheter of claim 6, wherein at least one of the conductive wires extends through the elongate tube to the at least one shock wave emitter and comprises a refractory metal.

8. The shock wave catheter of claim 1, comprising an optical fiber optically coupled to the at least one shock wave emitter.

9. The shock wave catheter of claim 1, comprising a radiopaque marker disposed proximate to the at least one shock wave emitter for viewing the at least one shock wave emitter.

10. The shock wave catheter of claim 1, comprising a first fluid lumen configured to fill the enclosure, and a second fluid lumen configured to remove gas bubbles from the enclosure that are generated during shock wave generation.

11. The shock wave catheter of claim 1, wherein the at least one shock wave emitter is configured to emit at least one distally directed shock wave when an energy pulse is supplied to the at least one shock wave emitter.

12. The shock wave catheter of claim 1, wherein an outer diameter of the shock wave catheter is between 0.25-1 mm.

13. The shock wave catheter of claim 1, wherein the distal tip is configured to maintain a position and orientation of the at least one shock wave emitter during use.

14. The shock wave catheter of claim 1, wherein the elongate tube comprises a variable pitch flat wire coil, a pitch of a proximal portion of the coil being greater than a pitch of a distal portion of the coil.

15. A system for treating a lesion of a body lumen, comprising:
the shock wave catheter of claim 1; and
a pulse generator coupled to the at least one shock wave emitter and configured to generate energy pulses to cause the at least one shock wave emitter to generate the at least one shock wave.

16. The system of claim 15, wherein the pulse generator is configured to generate the energy pulses with a frequency between 1 Hz and 5 Hz and a voltage between 0.5 kV and 10.0 kV.

17. The system of claim 15, wherein the pulse generator is configured to generate one or more laser pulses to cause the at least one shock wave emitter to generate the at least one shock wave.

18. The system of claim 15, wherein the system comprises a switch coupled to the core wire to control the deflection of the distal portion of the shock wave catheter.

19. The system of claim 15, comprising a control hub connected to a proximal portion of the elongate tube and configured to receive the core wire, the control hub comprising:
at least one fluid port connected to a lumen of the elongate tube via at least one opening in the elongate tube to aspirate and purge the lumen; and
a port that facilitates connection of the pulse generator to the at least one shock wave emitter.

20. The system of claim 19, wherein the control hub comprises at least one pressure seal enclosing the at least one opening of the elongate tube, and wherein the fluid port fluidly connects to a vacuum pressure source and to a conductive fluid source to (a) decrease pressure within at least one of the lumen of the elongate tube and the enclosure, and (b) subsequently draw conductive fluid into at least one of the lumen of the elongate tube and the enclosure.

21. A shock wave catheter for treating a lesion of a body lumen, the shock wave catheter comprising:
an elongate tube;
at least one shock wave emitter disposed distal to the elongate tube and configured to generate at least one shock wave;
a distal tip disposed at or proximate to a distal end of the at least one shock wave emitter;
an enclosure enclosing at least the at least one shock wave emitter;
a first fluid lumen configured to fill the enclosure; and
a second fluid lumen configured to remove gas bubbles from the enclosure that are generated during shock wave generation.

22. The shock wave catheter of claim 21, wherein at least a portion of the elongate tube comprises a coil, a plurality of slits, or a braided portion.

23. The shock wave catheter of claim 21, comprising a core wire extending within the elongate tube and terminating proximate to a distal end of the elongate tube, wherein the core wire is configured to control deflection of at least a distal portion of the shock wave catheter.

24. The shock wave catheter of claim 21, wherein the shock wave catheter does not include a guidewire lumen.

25. The shock wave catheter of claim 21, comprising a radiopaque marker disposed proximate to the at least one shock wave emitter for viewing the at least one shock wave emitter.

26. The shock wave catheter of claim 21, wherein the at least one shock wave emitter is configured to emit at least one distally directed shock wave when an energy pulse is supplied to the at least one shock wave emitter.

27. A system for treating a lesion of a body lumen, comprising:
the shock wave catheter of claim 21; and
a pulse generator coupled to the at least one shock wave emitter and configured to generate energy pulses to cause the at least one shock wave emitter to generate the at least one shock wave.

28. The system of claim 27, wherein the shock wave catheter comprises a core wire extending within the elongate tube and terminating proximate to a distal end of the elongate tube, and the system comprises a switch coupled to the core wire to control deflection of a distal portion of the shock wave catheter.

29. The system of claim 27, comprising a control hub connected to a proximal portion of the elongate tube and configured to receive the core wire, the control hub comprising:
at least one fluid port connected to the first fluid lumen of the elongate tube via at least one opening in the elongate tube to aspirate and purge the first fluid lumen; and
a port that facilitates connection of the pulse generator to the at least one shock wave emitter.

30. The system of claim 29, wherein the control hub comprises at least one pressure seal enclosing the at least one opening of the elongate tube, and wherein the fluid port fluidly connects to a vacuum pressure source and to a conductive fluid source to (a) decrease pressure within at least one of the first fluid lumen and the enclosure, and (b) subsequently draw conductive fluid into the first fluid lumen.

* * * * *